(12) United States Patent
Duffy et al.

(10) Patent No.: US 8,182,763 B2
(45) Date of Patent: May 22, 2012

(54) RACK FOR SAMPLE TUBES AND REAGENT HOLDERS

(75) Inventors: Patrick Duffy, Whitmore Lake, MI (US); Kerry Wilson, Elkhart, IN (US); Kalyan Handique, Ypsilanti, MI (US); Jeff Williams, Chelsea, MI (US)

(73) Assignee: HandyLab, Inc., Ann Arbor, MI (US)

( * ) Notice: Subject to any disclaimer, the term of this patent is extended or adjusted under 35 U.S.C. 154(b) by 0 days.

(21) Appl. No.: 12/178,584

(22) Filed: Jul. 23, 2008

(65) Prior Publication Data
US 2009/0136386 A1    May 28, 2009

Related U.S. Application Data

(63) Continuation-in-part of application No. 12/173,023, filed on Jul. 14, 2008, and a continuation-in-part of application No. 12/218,498, filed on Jul. 14, 2008.

(60) Provisional application No. 60/959,437, filed on Jul. 13, 2007.

(51) Int. Cl.
*B01L 9/06* (2006.01)

(52) U.S. Cl. ......... 422/500; 422/68.1; 422/50; 422/401; 422/501; 422/519; 211/74; 211/194; 211/60.1

(58) Field of Classification Search .............. 422/68.1, 422/99, 102, 104, 50, 401, 402, 403, 404, 422/500, 501, 519; 211/60.1, 74
See application file for complete search history.

(56) References Cited

U.S. PATENT DOCUMENTS

| 1,434,314 | A | * | 10/1922 | Raich | 220/757 |
|---|---|---|---|---|---|
| 1,616,419 | A | | 2/1927 | Wilson | |
| 1,733,401 | A | | 8/1930 | Lovekin | |
| 3,528,449 | A | | 9/1970 | Witte et al. | |
| 3,985,649 | A | | 10/1976 | Eddelman | |
| 4,018,089 | A | | 4/1977 | Dzula et al. | |
| 4,018,652 | A | | 4/1977 | Lanham et al. | |
| 4,038,192 | A | | 7/1977 | Serur | |
| 4,055,395 | A | | 10/1977 | Honkawa et al. | |
| D249,706 | S | | 9/1978 | Adamski | |
| 4,139,005 | A | | 2/1979 | Dickey | |

(Continued)

FOREIGN PATENT DOCUMENTS

CA    2294819    1/1999

(Continued)

OTHER PUBLICATIONS

Bollet, C. et al., "A simple method for the isolation of chromosomal DNA from Gram positive or acid-fast bacteria", Nucleic Acids Research, vol. 19, No. 8 (1991), p. 1955.

(Continued)

*Primary Examiner* — In Suk Bullock
*Assistant Examiner* — Sharon Pregler
(74) *Attorney, Agent, or Firm* — Knobbe Martens Olson & Bear LLP

(57) ABSTRACT

A rack for holding samples and various reagents, wherein the rack may be used for loading the samples and reagents prior to using the reagents. The rack accepts complementary reagent holders, each of which contain a set of reagents for carrying out a predetermined processing operation, such as preparing biological samples for amplifying and detecting polynucleotides extracted from the samples.

28 Claims, 18 Drawing Sheets

U.S. PATENT DOCUMENTS

| | | |
|---|---|---|
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,654,127 A | 3/1987 | Baker et al. |
| 4,673,657 A | 6/1987 | Christian |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,798,693 A | 1/1989 | Mase et al. |
| 4,800,022 A | 1/1989 | Leonard |
| 4,841,786 A | 6/1989 | Schulz |
| D302,294 S | 7/1989 | Hillman |
| 4,895,650 A | 1/1990 | Wang |
| 4,919,829 A | 4/1990 | Gates |
| 4,921,809 A | 5/1990 | Schiff et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman et al. |
| 4,967,950 A | 11/1990 | Legg et al. |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,223,226 A | 6/1993 | Whittmer et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic, Jr. |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,818 A | 11/1996 | Kain et al. |
| 5,580,523 A | 12/1996 | Bard |
| 5,582,884 A | 12/1996 | Ball et al. |
| 5,585,069 A | 12/1996 | Zanzucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |
| 5,646,039 A | 7/1997 | Northrup et al. |
| 5,647,994 A | 7/1997 | Tuunanen et al. |
| 5,651,839 A | 7/1997 | Rauf |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce |
| 5,700,637 A | 12/1997 | Southern |
| 5,705,813 A | 1/1998 | Apffel et al. |
| 5,726,026 A | 3/1998 | Wilding et al. |
| 5,726,404 A | 3/1998 | Brody |
| 5,726,944 A | 3/1998 | Taft et al. |
| 5,731,212 A | 3/1998 | Gavin et al. |
| 5,744,366 A | 4/1998 | Kricka et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |

| | | | | | | |
|---|---|---|---|---|---|---|
| 5,787,032 A | 7/1998 | Heller et al. | | 6,010,608 A | 1/2000 | Ramsey |
| 5,788,814 A | 8/1998 | Sun et al. | | 6,010,627 A | 1/2000 | Hood, III |
| 5,800,690 A | 9/1998 | Chow et al. | | 6,012,902 A | 1/2000 | Parce |
| 5,804,436 A | 9/1998 | Okun et al. | | D420,747 S | 2/2000 | Dumitrescu et al. |
| D399,959 S | 10/1998 | Prokop et al. | | D421,130 S | 2/2000 | Cohen et al. |
| 5,827,481 A | 10/1998 | Bente et al. | | 6,024,920 A | 2/2000 | Cunanan |
| 5,842,106 A | 11/1998 | Thaler et al. | | D421,653 S | 3/2000 | Purcell |
| 5,842,787 A | 12/1998 | Kopf-Sill et al. | | 6,033,546 A | 3/2000 | Ramsey |
| 5,846,396 A | 12/1998 | Zanzucchi et al. | | 6,043,080 A | 3/2000 | Lipshutz et al. |
| 5,849,208 A | 12/1998 | Hayes et al. | | 6,046,056 A | 4/2000 | Parce et al. |
| 5,849,486 A | 12/1998 | Heller et al. | | 6,048,734 A | 4/2000 | Burns et al. |
| 5,849,489 A | 12/1998 | Heller | | 6,054,034 A | 4/2000 | Soane et al. |
| 5,849,598 A | 12/1998 | Wilson et al. | | 6,054,277 A | 4/2000 | Furcht et al. |
| 5,852,495 A | 12/1998 | Parce | | 6,056,860 A | 5/2000 | Amigo et al. |
| 5,856,174 A | 1/1999 | Lipshutz et al. | | 6,057,149 A | 5/2000 | Burns et al. |
| 5,858,187 A | 1/1999 | Ramsey et al. | | 6,062,261 A | 5/2000 | Jacobson et al. |
| 5,858,188 A | 1/1999 | Soane et al. | | 6,063,341 A * | 5/2000 | Fassbind et al. ............... 422/102 |
| 5,863,502 A | 1/1999 | Southgate et al. | | 6,063,589 A | 5/2000 | Kellogg et al. |
| 5,863,708 A | 1/1999 | Zanzucchi et al. | | 6,071,478 A | 6/2000 | Chow |
| 5,863,801 A | 1/1999 | Southgate et al. | | 6,074,725 A | 6/2000 | Kennedy |
| 5,866,345 A | 2/1999 | Wilding et al. | | 6,074,827 A | 6/2000 | Nelson et al. |
| 5,869,004 A | 2/1999 | Parce et al. | | D428,497 S | 7/2000 | Lapeus et al. |
| 5,872,010 A | 2/1999 | Karger et al. | | 6,086,740 A | 7/2000 | Kennedy |
| 5,874,046 A | 2/1999 | Megerle | | 6,096,509 A | 8/2000 | Okun et al. |
| 5,876,675 A | 3/1999 | Kennedy | | 6,100,541 A | 8/2000 | Nagle et al. |
| 5,880,071 A | 3/1999 | Parce et al. | | 6,102,897 A | 8/2000 | Lang |
| 5,882,465 A | 3/1999 | McReynolds | | 6,103,537 A | 8/2000 | Ullman et al. |
| 5,883,211 A | 3/1999 | Sassi et al. | | 6,106,685 A | 8/2000 | McBride et al. |
| 5,885,432 A | 3/1999 | Hooper et al. | | 6,110,343 A | 8/2000 | Ramsey et al. |
| 5,885,470 A | 3/1999 | Parce et al. | | 6,123,205 A | 9/2000 | Dumitrescu et al. |
| 5,895,762 A | 4/1999 | Greenfield et al. | | 6,123,798 A | 9/2000 | Gandhi et al. |
| 5,900,130 A | 5/1999 | Benregnu et al. | | 6,130,098 A | 10/2000 | Handique et al. |
| 5,912,124 A | 6/1999 | Kumar | | 6,132,580 A | 10/2000 | Mathies et al. |
| 5,912,134 A | 6/1999 | Shartle | | 6,132,684 A * | 10/2000 | Marino ........................ 422/104 |
| 5,916,522 A | 6/1999 | Boyd et al. | | 6,133,436 A | 10/2000 | Koster et al. |
| 5,916,776 A | 6/1999 | Kumar | | D433,759 S | 11/2000 | Mathis et al. |
| 5,919,646 A | 7/1999 | Okun et al. | | 6,143,250 A | 11/2000 | Tajima |
| 5,919,711 A | 7/1999 | Boyd et al. | | 6,149,787 A | 11/2000 | Chow et al. |
| 5,922,591 A | 7/1999 | Anderson et al. | | 6,156,199 A | 12/2000 | Zuk, Jr. |
| 5,927,547 A | 7/1999 | Papen et al. | | 6,158,269 A | 12/2000 | Dorenkott et al. |
| 5,928,880 A | 7/1999 | Wilding et al. | | 6,167,910 B1 | 1/2001 | Chow |
| 5,929,208 A | 7/1999 | Heller et al. | | 6,168,948 B1 | 1/2001 | Anderson et al. |
| D413,391 S | 8/1999 | Lapeus et al. | | 6,171,850 B1 | 1/2001 | Nagle et al. |
| 5,932,799 A | 8/1999 | Moles | | 6,174,675 B1 | 1/2001 | Chow et al. |
| 5,935,401 A | 8/1999 | Amigo | | D438,311 S | 2/2001 | Yamanishi et al. |
| 5,939,291 A | 8/1999 | Loewy et al. | | 6,190,619 B1 | 2/2001 | Kilcoin et al. |
| 5,942,443 A | 8/1999 | Parce et al. | | D438,632 S | 3/2001 | Miller |
| D413,677 S | 9/1999 | Dumitrescu et al. | | D438,633 S | 3/2001 | Miller |
| 5,948,227 A | 9/1999 | Dubrow | | 6,197,595 B1 | 3/2001 | Anderson et al. |
| 5,955,028 A | 9/1999 | Chow | | 6,211,989 B1 | 4/2001 | Wulf et al. |
| 5,955,029 A | 9/1999 | Wilding et al. | | 6,213,151 B1 | 4/2001 | Jacobson et al. |
| 5,957,579 A | 9/1999 | Kopf-Sill et al. | | 6,221,600 B1 | 4/2001 | MacLeod et al. |
| 5,958,203 A | 9/1999 | Parce et al. | | 6,228,635 B1 | 5/2001 | Armstrong et al. |
| 5,958,694 A | 9/1999 | Nikiforov | | 6,235,175 B1 | 5/2001 | Dubrow et al. |
| 5,959,221 A * | 9/1999 | Boyd et al. .................... 422/104 | | 6,235,313 B1 | 5/2001 | Mathiowitz et al. |
| 5,959,291 A | 9/1999 | Jensen | | 6,235,471 B1 | 5/2001 | Knapp et al. |
| 5,964,995 A | 10/1999 | Nikiforov et al. | | 6,236,581 B1 | 5/2001 | Lines et al. |
| 5,964,997 A | 10/1999 | McBride | | 6,251,343 B1 | 6/2001 | Dubrow et al. |
| 5,965,001 A | 10/1999 | Chow et al. | | 6,254,826 B1 * | 7/2001 | Acosta et al. ................... 422/65 |
| 5,965,410 A | 10/1999 | Chow et al. | | 6,259,635 B1 | 7/2001 | Torelli et al. |
| 5,965,886 A | 10/1999 | Sauer et al. | | 6,261,431 B1 | 7/2001 | Mathies et al. |
| 5,972,187 A | 10/1999 | Parce et al. | | 6,267,858 B1 | 7/2001 | Parce et al. |
| 5,973,138 A | 10/1999 | Collis | | D446,306 S | 8/2001 | Ochi et al. |
| D417,009 S | 11/1999 | Boyd | | 6,271,021 B1 | 8/2001 | Burns et al. |
| 5,976,336 A | 11/1999 | Dubrow et al. | | 6,274,089 B1 | 8/2001 | Chow et al. |
| 5,980,704 A | 11/1999 | Cherukuri et al. | | 6,280,967 B1 | 8/2001 | Ransom et al. |
| 5,980,719 A | 11/1999 | Cherukuri et al. | | 6,281,008 B1 | 8/2001 | Komai et al. |
| 5,981,735 A | 11/1999 | Thatcher et al. | | 6,284,113 B1 | 9/2001 | Bjornson et al. |
| 5,989,402 A | 11/1999 | Chow et al. | | 6,287,254 B1 | 9/2001 | Dodds |
| 5,992,820 A | 11/1999 | Fare et al. | | 6,287,774 B1 | 9/2001 | Kikiforov |
| 5,993,611 A | 11/1999 | Moroney, III et al. | | 6,291,248 B1 | 9/2001 | Haj-Ahmad |
| 5,993,750 A | 11/1999 | Ghosh et al. | | 6,294,063 B1 | 9/2001 | Becker et al. |
| 5,997,708 A | 12/1999 | Craig | | 6,302,134 B1 | 10/2001 | Kellogg et al. |
| 6,001,229 A | 12/1999 | Ramsey | | 6,302,304 B1 | 10/2001 | Spencer |
| 6,001,231 A | 12/1999 | Kopf-Sill | | 6,303,343 B1 | 10/2001 | Kopf-Sill |
| 6,001,307 A | 12/1999 | Naka et al. | | 6,306,273 B1 | 10/2001 | Wainright et al. |
| 6,004,515 A | 12/1999 | Parce et al. | | 6,306,590 B1 | 10/2001 | Mehta et al. |
| 6,007,690 A | 12/1999 | Nelson et al. | | 6,319,469 B1 | 11/2001 | Mian et al. |
| 6,010,607 A | 1/2000 | Ramsey | | 6,322,683 B1 | 11/2001 | Wolk et al. |

| Patent | Date | Inventor |
|---|---|---|
| 6,326,083 B1 | 12/2001 | Yang et al. |
| 6,326,211 B1 | 12/2001 | Anderson et al. |
| 6,337,435 B1 | 1/2002 | Chu et al. |
| 6,353,475 B1 | 3/2002 | Jensen et al. |
| 6,358,387 B1 | 3/2002 | Kopf-Sill et al. |
| 6,366,924 B1 | 4/2002 | Parce |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Majer et al. |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-Sill |
| 6,425,972 B1 | 7/2002 | Mcreynolds |
| D461,906 S | 8/2002 | Pham |
| 6,428,987 B2 | 8/2002 | Franzen |
| 6,430,512 B1 | 8/2002 | Gallagher |
| 6,432,366 B2 * | 8/2002 | Ruediger et al. ............... 422/100 |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | Mcreynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 * | 8/2003 | Tajima .......................... 422/102 |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| D482,796 S | 11/2003 | Oyama et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |
| D515,707 S | 2/2006 | Sinohara et al. |

| | | |
|---|---|---|
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | da Silva |
| 7,069,952 B1 | 7/2006 | Mcreynolds et al. |
| 7,099,778 B2 | 8/2006 | Chien |
| D528,215 S | 9/2006 | Malmsäter |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skold |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,330 B2 | 10/2007 | Chow et al. |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| 7,553,671 B2 * | 6/2009 | Sinclair et al. ............... 422/104 |
| D596,312 S | 7/2009 | Giraud et al. |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,704,735 B2 | 4/2010 | Facer et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| 7,867,776 B2 | 1/2011 | Kennedy et al. |
| 7,892,819 B2 | 2/2011 | Wilding et al. |
| 2001/0023848 A1 | 9/2001 | Gjerde et al. |
| 2001/0038450 A1 | 11/2001 | McCaffrey et al. |
| 2001/0046702 A1 | 11/2001 | Schembri |
| 2001/0055765 A1 | 12/2001 | O'Keefe et al. |
| 2002/0001848 A1 | 1/2002 | Bedingham et al. |
| 2002/0009015 A1 | 1/2002 | Laugharn, Jr. et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0060156 A1 | 5/2002 | Mathies et al. |
| 2002/0068357 A1 | 6/2002 | Mathies et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0169518 A1 | 11/2002 | Luoma et al. |
| 2002/0187557 A1 | 12/2002 | Hobbs et al. |
| 2003/0019522 A1 | 1/2003 | Parunak |
| 2003/0049833 A1 | 3/2003 | Chen et al. |
| 2003/0070677 A1 | 4/2003 | Handique et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0199081 A1 | 10/2003 | Wilding et al. |
| 2003/0799081 | 10/2003 | Wilding et al. |
| 2003/0211517 A1 | 11/2003 | Carulli et al. |
| 2004/0014238 A1 | 1/2004 | Krug et al. |
| 2004/0029258 A1 | 2/2004 | Heaney et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0240097 A1 | 12/2004 | Evans |
| 2005/0009174 A1 | 1/2005 | Nikiforov et al. |
| 2005/0048540 A1 | 3/2005 | Inami et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0133370 A1 | 6/2005 | Park et al. |
| 2005/0135655 A1 | 6/2005 | Kopf-Sill et al. |
| 2005/0152808 A1 | 7/2005 | Ganesan |
| 2005/0170362 A1 | 8/2005 | Wada et al. |
| 2005/0202470 A1 | 9/2005 | Sundberg et al. |
| 2005/0202504 A1 | 9/2005 | Anderson et al. |
| 2005/0208676 A1 | 9/2005 | Kahatt |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |

| | | | |
|---|---|---|---|
| 2006/0165559 A1 | 7/2006 | Greenstein et al. | |
| 2006/0166233 A1 | 7/2006 | Wu et al. | |
| 2006/0177376 A1 | 8/2006 | Tomalia et al. | |
| 2006/0183216 A1 | 8/2006 | Handique | |
| 2006/0207944 A1 | 9/2006 | Siddiqi | |
| 2006/0246493 A1 | 11/2006 | Jensen et al. | |
| 2006/0246533 A1 | 11/2006 | Fathollahi et al. | |
| 2007/0004028 A1 | 1/2007 | Lair et al. | |
| 2007/0009386 A1 | 1/2007 | Padmanabhan et al. | |
| 2007/0020699 A1 | 1/2007 | Carpenter et al. | |
| 2007/0026421 A1 | 2/2007 | Sundberg et al. | |
| 2007/0042441 A1 | 2/2007 | Masters et al. | |
| 2007/0092901 A1 | 4/2007 | Ligler et al. | |
| 2007/0098600 A1 | 5/2007 | Kayyem et al. | |
| 2007/0099200 A1 | 5/2007 | Chow et al. | |
| 2007/0154895 A1 | 7/2007 | Spaid et al. | |
| 2007/0177147 A1 | 8/2007 | Parce | |
| 2007/0178607 A1 | 8/2007 | Prober et al. | |
| 2007/0184463 A1 | 8/2007 | Molho et al. | |
| 2007/0184547 A1 | 8/2007 | Handique et al. | |
| 2007/0196238 A1 | 8/2007 | Kennedy et al. | |
| 2007/0199821 A1 | 8/2007 | Chow | |
| 2007/0218459 A1 | 9/2007 | Miller et al. | |
| 2007/0231213 A1 | 10/2007 | Prabhu et al. | |
| 2007/0261479 A1 | 11/2007 | Spaid et al. | |
| 2007/0269861 A1 | 11/2007 | Williams et al. | |
| 2007/0292941 A1 | 12/2007 | Handique et al. | |
| 2008/0000774 A1 | 1/2008 | Park et al. | |
| 2008/0050804 A1 | 2/2008 | Handique et al. | |
| 2008/0075634 A1* | 3/2008 | Herchenbach et al. | 422/104 |
| 2008/0090244 A1 | 4/2008 | Knapp et al. | |
| 2008/0118987 A1 | 5/2008 | Eastwood et al. | |
| 2008/0124723 A1 | 5/2008 | Dale et al. | |
| 2008/0149840 A1 | 6/2008 | Handique et al. | |
| 2008/0160601 A1 | 7/2008 | Handique | |
| 2008/0182301 A1 | 7/2008 | Handique et al. | |
| 2008/0192254 A1 | 8/2008 | Kim et al. | |
| 2008/0247914 A1 | 10/2008 | Edens et al. | |
| 2008/0262213 A1 | 10/2008 | Wu et al. | |
| 2009/0047713 A1 | 2/2009 | Handique | |
| 2009/0129978 A1* | 5/2009 | Wilson et al. | 422/102 |
| 2009/0130719 A1 | 5/2009 | Handique | |
| 2009/0130745 A1 | 5/2009 | Williams et al. | |
| 2009/0131650 A1 | 5/2009 | Brahmasandra et al. | |
| 2009/0134069 A1 | 5/2009 | Handique | |
| 2009/0136385 A1 | 5/2009 | Handique et al. | |
| 2009/0136386 A1 | 5/2009 | Duffy et al. | |
| 2009/0155123 A1 | 6/2009 | Williams et al. | |
| 2009/0221059 A1 | 9/2009 | Williams et al. | |
| 2009/0223925 A1 | 9/2009 | Morse et al. | |
| 2010/0009351 A1 | 1/2010 | Brahmasandra et al. | |

FOREIGN PATENT DOCUMENTS

| | | |
|---|---|---|
| DE | 19929734 | 12/1999 |
| EP | 0766256 | 4/1997 |
| FR | 2672301 | 8/1992 |
| FR | 2795426 | 12/2000 |
| JP | 58212921 A | 12/1983 |
| JP | H07-290706 | 11/1995 |
| JP | 2001-515216 | 9/2001 |
| WO | WO 88/06633 | 9/1988 |
| WO | WO 92/05443 | 4/1992 |
| WO | WO 98/00231 | 1/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/078845 | 10/2002 |
| WO | WO 03/012325 | 2/2003 |
| WO | WO 03/012406 | 2/2003 |
| WO | WO 03/055605 | 7/2003 |
| WO | WO 2004/007081 | 1/2004 |
| WO | WO 2004/074848 | 9/2004 |
| WO | WO 2005/011867 | 2/2005 |
| WO | WO 2005/108620 | 11/2005 |
| WO | WO 2006/079082 | 7/2006 |
| WO | WO 2008/060604 | 5/2008 |
| WO | WO 2009/012185 | 1/2009 |

OTHER PUBLICATIONS

Brahmassandra, et al., On-Chip DNA Detection in Microfabricated Separation Systems, Part of the SPIE Conference on Microfludic Devices and Systems, 1998, Santa Clara, California, vol. 3515, pp. 242-251.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles, et al., "Sample Filtration, Concentration, and Separation Integrated on Microfluidic Devices" Analytical Chemistry (American Chemical Society), vol. 75 No. 11: pp. 2761-2767, year: 2003.

Burns et al., "An Integrated Nanoliter DNA Analysis Device", Science 282:484-487 (1998).

Carlen et al., "Paraffin Actuated Surface Micromachined Valve," in IEEE MEMS 2000 Conference, p. 381-385, Miyazaki, Japan, Jan. 2000.

Chung, Y. et al., "Microfluidic chip for high efficiency DNA extraction", Miniaturisation for Chemistry, Biology & Bioengineering, vol. 4, No. 2 (Apr. 2004), pp. 141-147.

Handique K., et al., On-Chip Thermopneumatic Pressure for Discrete Drop Pumping, Analytical Chemistry, American Chemical Society, Apr. 15, 2001, vol. 73, No. 8, 1831-1838.

Handique, K. et al, "Microflidic flow control using selective hydrophobic patterning", SPIE, vol. 3224, pp. 185-194 (1997).

Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique, K. et al., "Mathematical Modeling of Drop Mixing in a Slit-Type Micochannel", J. Micromech. Microeng., 11:548-554 (2001).

Handique, K. et al., "Nanoliter Liquid Metering in Microchannels Using Hydrophobic Patterns", Anal. Chem., 72:4100-4109 (2000).

He, et al., Microfabricated Filters for Microfludic Analytical Systems, Analytical Chemistry, American Chemical Society, 1999, vol. 71, No. 7, pp. 1464-1468.

Ibrahim, et al., Real-Time Microchip PCR for Detecting Single-Base Differences in Viral and Human DNA, Analytical Chemistry, American Chemical Society, 1998, vol. 70, No. 9, pp. 2013-2017.

Khandurina, et al., Microfabricated Porous Membrane Structure for Sample Concentration and Electrophoretic Analysis, Analytical Chemistry American Chemical Society, 1999, vol. 71, No. 9, pp. 1815-1819.

Kopp, et al., Chemical Amplification: Continuous-Flow PCR on a Chip, www.sciencemag.org, 1998, vol. 280, pp. 1046-1048.

Kutter, et al., Solid Phase Extraction on Microfludic Devices, J. Microcolumn Separations, John Wiley & Sons, Inc., 2000, vol. 12, No. 2, pp. 93-97.

Lagally, et al., Single-Molecule Dna Amplification and Analysis in an Integrated Microfluidic Device, Analytical Chemistry, American Chemical Society, 2001, vol. 73, No. 3 pp. 565-570.

Livache, T. et al., "Polypyrrole DNA chip on a Silicon Device: Example of Hepatitis C Virus Genotyping", Analytical Biochemistry, vol. 255 (1998), pp. 188-194.

Northrup, et al., A Miniature Analytical Instrument for Nucleic Acids Based on Micromachined Silicon Reaction Chambers, Analytical Chemistry, American Chemical Society, 1998, vol. 70, No. 5, pp. 918-922.

Oleschuk, et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.

Orchid BioSciences, Inc., www.orchid.com, Jul. 6, 2001.

Roche, et al. "Ectodermal commitment of insulin-producing cells derived from mouse embryonic stem cells" Faseb J (2005) 19: 1341-1343.

Ross, et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner, M. A. et al., Chip PCR.I. Surface Passivation of Microfabricated Silicon-Glass Chips for PCR, Nucleic Acids Research, Oxford University Press, 1996, vol. 24, No. 2, 375-379.

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Waters, et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl, et al., Microfluidic Diffusion-Based Separation and Detection, www.sciencemag.org, 1999, vol. 283, pp. 346-347.

Yoza, Brandon et al., DNA extraction using bacterial magnetic particles modified with hyperbranched polyamidoamine dendrimer, Mar. 20, 2003, vol. 101, No. 3, 219-228.

Yoza, et al., "Fully Automated DNA Extraction fro Blood Using Magnetic Particles Modified with a Hyperbranched Polyamidomine Dendrimer", Journal of Bioscience and Bioengineering, 95(1):21-26, 2003.

* cited by examiner

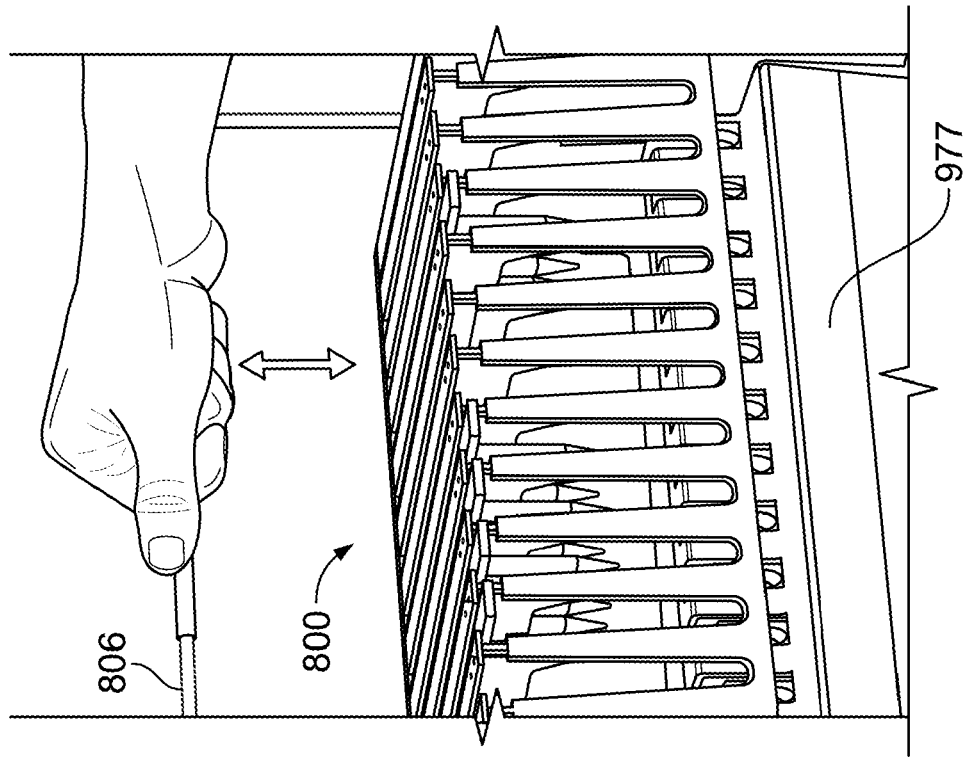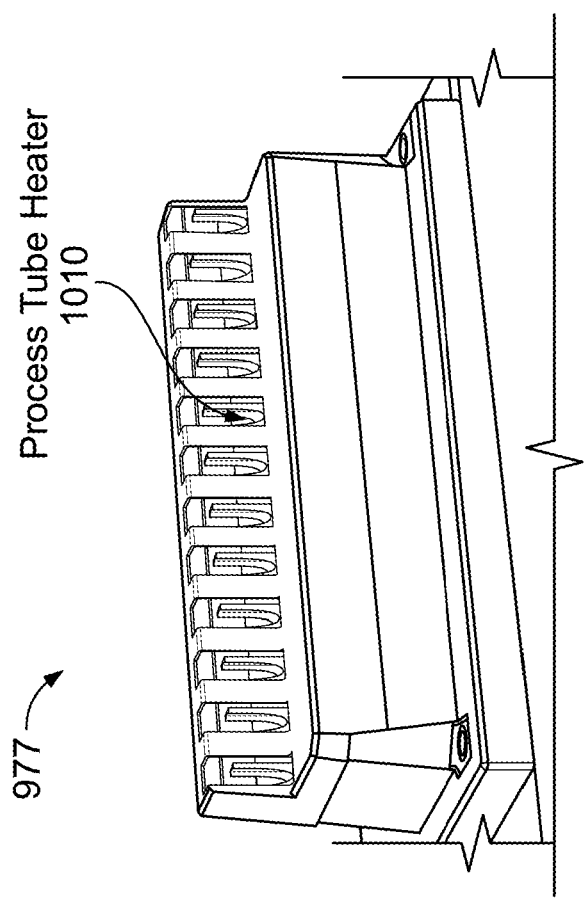
FIG. 2

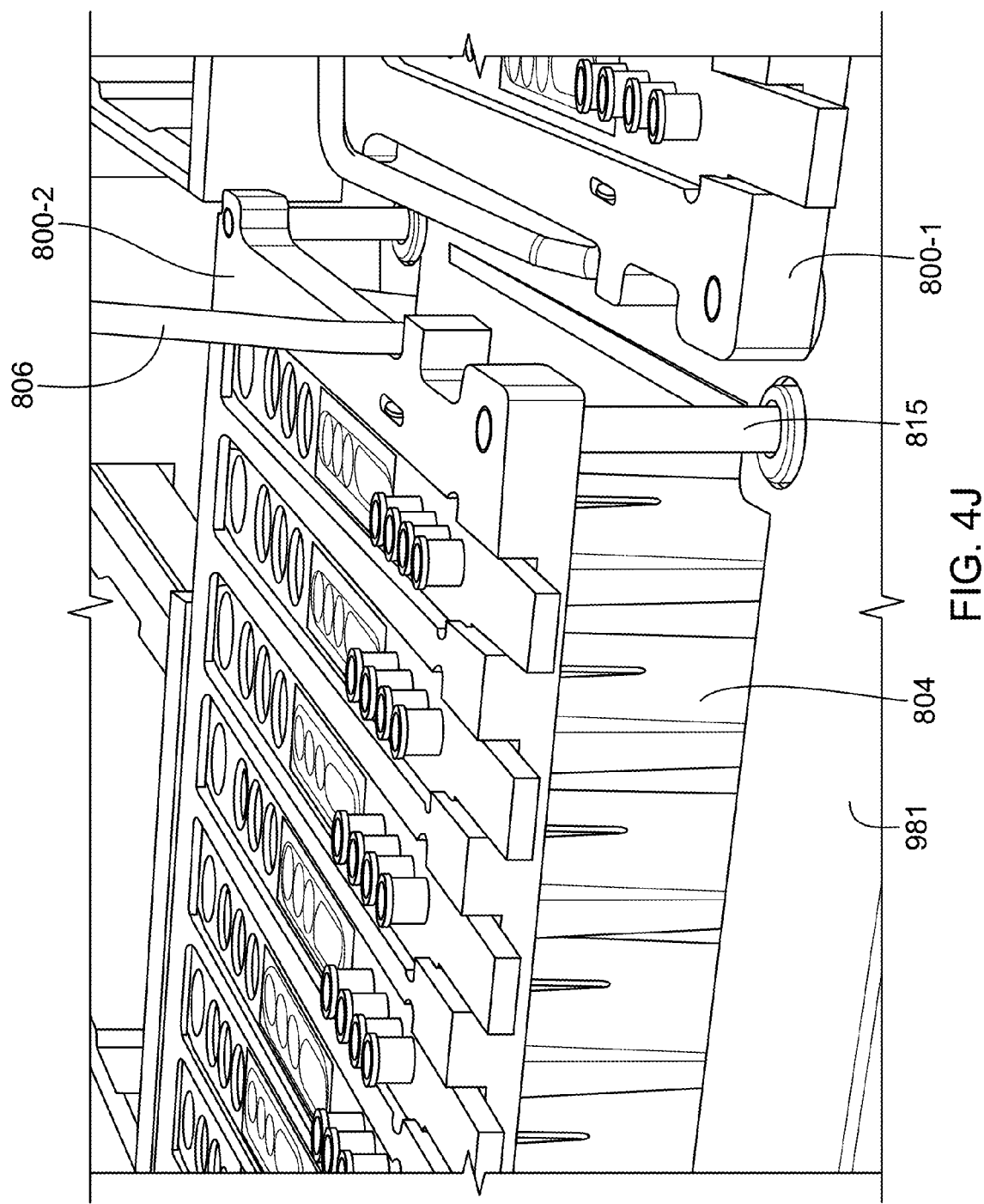

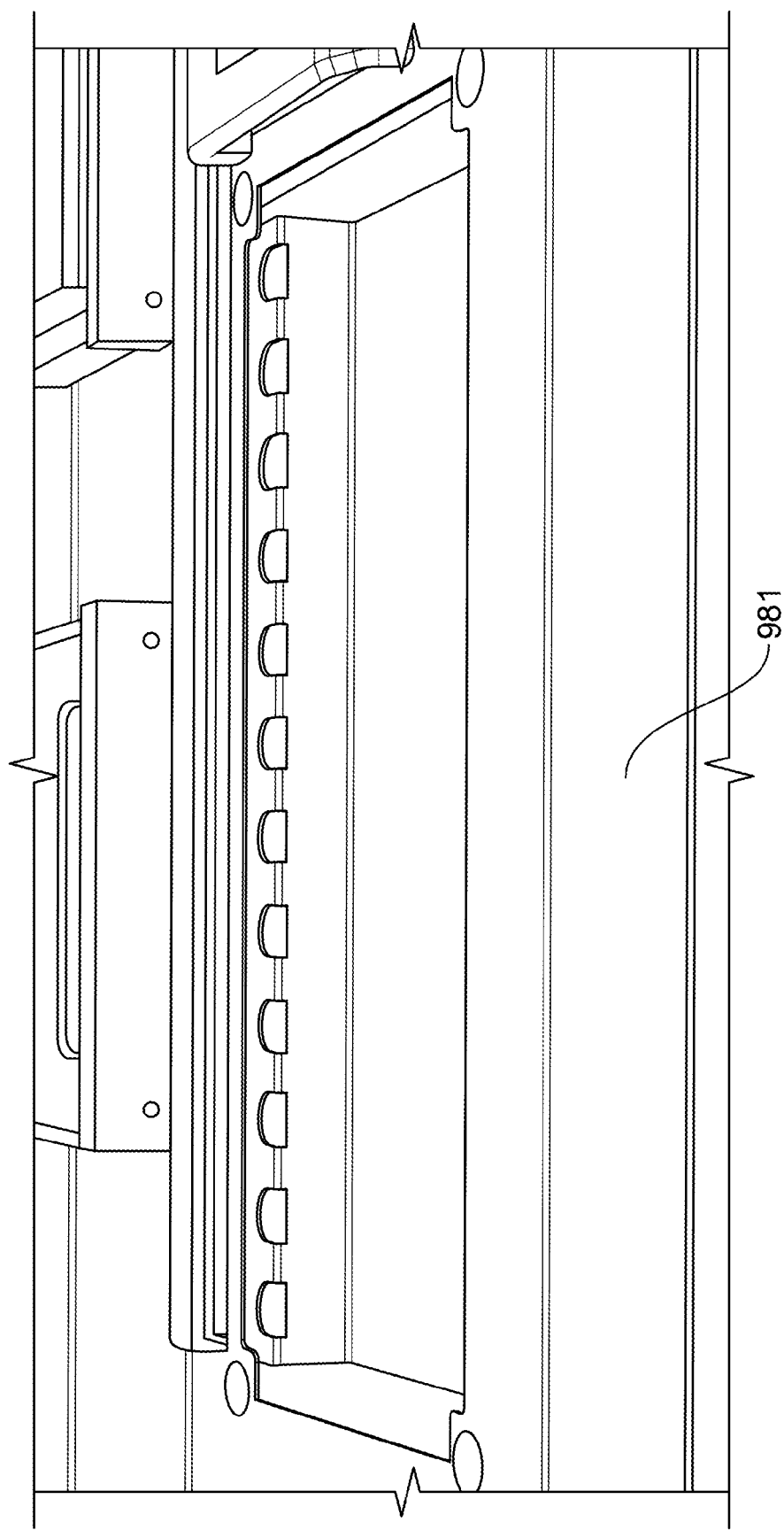

RACK FOR SAMPLE TUBES AND REAGENT HOLDERS

CLAIM OF PRIORITY

This application is a continuation-in-part of U.S. patent application Ser. Nos. 12/173,023 and 12/218,498, both filed on Jul. 14, 2008, which claim benefit of priority to U.S. provisional Patent Application Ser. No. 60/959,437, filed Jul. 13, 2007, all of which are incorporated herein by reference in their entireties.

TECHNICAL FIELD

The technology described herein generally relates to racks for holding samples and various reagents, wherein the rack may be used for loading the samples and reagents prior to using the reagents. The technology more particularly relates to racks that accept complementary reagent holders each of which contain a set of reagents for carrying out a predetermined processing operation, such as preparing biological samples for amplifying and detecting polynucleotides extracted from the samples.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss or mishandling. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using PCR to amplify a vector of interest. Once amplified, the presence of a nucleotide of interest from the sample needs to be determined unambiguously. Preparing samples for PCR is currently a time-consuming and labor intensive step, though not one requiring specialist skills, and could usefully be automated. By contrast, steps such as PCR and nucleotide detection have customarily only been within the compass of specially trained individuals having access to specialist equipment.

Sample preparation is labor intensive in part because of the number of reagents required, and the need for multiple liquid transfer (e.g., pipetting) operations. Furthermore, the reagents required are of sufficient variety that they typically require different handling from one another and are available from different vendors. Even where reagents can be collected together in a single holder and made ready for use, such as described in copending application Ser. No. 12/218,416, filed by ExpressMail on Jul. 14, 2008 (and entitled "Reagent Tube, Reagent Holder, and Kits Containing Same", in the name of Wilson, et al.) and incorporated herein by reference, it would be beneficial to be able to set up a number of holders for use in batches, and to make them available to liquid dispensing tools that can operate on holders in parallel.

The discussion of the background herein is included to explain the context of the inventions described herein. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

A rack, comprising: a housing; a plurality of lanes in the housing, and wherein each lane of the plurality of lanes comprises: a first location configured to accept a sample tube; and a second location, configured to accept a reagent holder; and a registration member complementary to a receiving bay of a diagnostic apparatus.

A rack, wherein the registration member comprises two or more positioning pins configured to: ensure that the rack can only be placed in the diagnostic apparatus in a single orientation; and provide stability for the rack when placed in the diagnostic apparatus.

A rack configured to receive a plurality of reagent holders, and to receive a plurality of sample tubes, wherein the reagent holders are in one-to-one correspondence with the sample tubes, and wherein the reagent holders each contain sufficient reagents to extract polynucleotides from the sample and place the polynucleotides into a PCR-ready form, and wherein the rack is configured to be insertable into, and removable from, an apparatus that carries out PCR on the PCR-ready polynucleotides.

A method of carrying out sample preparation on multiple samples in parallel, wherein reagents for carrying out preparation on each sample are contained in respective reagent holders, the holders being supported by a rack, as further described herein. The method, can be carried out automatically by a diagnostic apparatus in which the rack is situated, or can be carried out manually, when the rack is positioned on a horizontal surface, e.g., a laboratory benchtop.

BRIEF DESCRIPTION OF THE DRAWINGS

FIG. 2 shows perspective views of a heater unit and the rack of FIG. 1 positioned in conjunction with the heater unit.

FIGS. 4A-4K show various views of the rack of FIG. 3.

FIG. 5 shows an area of a diagnostic apparatus configured to accept a rack of FIG. 3.

Like reference numerals in the various drawings indicate like elements.

DETAILED DESCRIPTION

Figure 1:
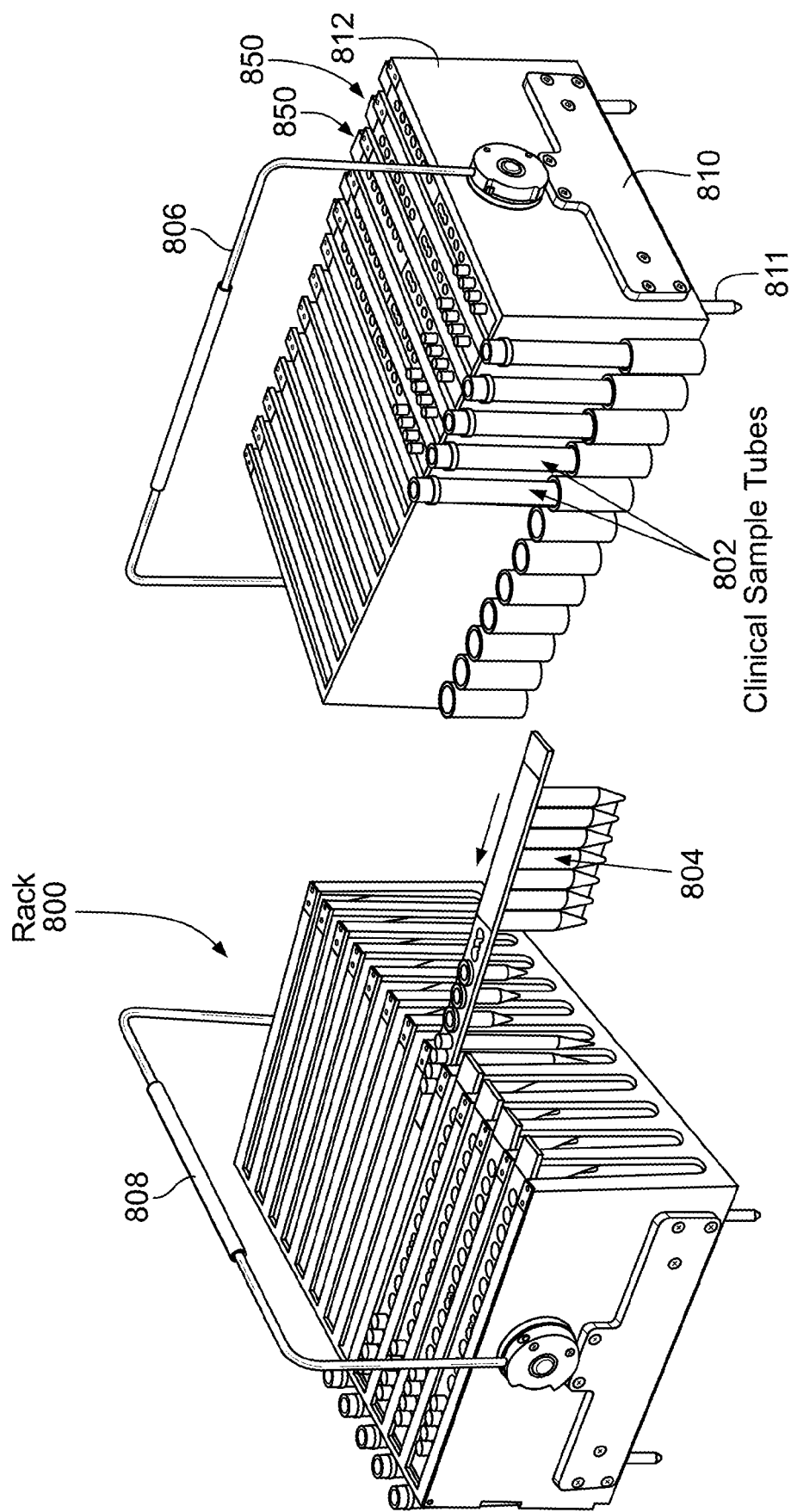
FIG. 1 shows perspective views of an exemplary rack for samples and reagent holders.

Described herein are racks for supporting, carrying, and transporting reagents for various purposes, in particular in connection with sample preparation in a clinical context. The rack permits placement of one or more sample tubes and one or more corresponding holders of reagents, such as analyte specific reagents (ASR's) and/or sample preparation reagents. The samples and holders, when so placed, are positioned to carry out liquid dispensing processes, associated with sample preparation such as for PCR, that minimize cross-sample contamination but permit multiple PCR preparations to be performed from multiple clinical samples, in batches, or in parallel. The racks are configured for use in an automated preparatory apparatus that can carry out sample preparation on samples in more than one holder positioned in a rack simultaneously.

The racks as described herein find particular application to analyzing any nucleic acid containing sample for any purpose, including but not limited to genetic testing, and clinical testing for various infectious diseases in humans.

In various embodiments, preparation of a PCR-ready sample for use in subsequent diagnosis, can include one or more of the following steps: contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid). In some embodiments, the PCR reagent mixture can be in the form of one or more lyophilized pellets, as stored in a container on a reagent holder, and the method can further include reconstituting the PCR pellet with liquid to create a PCR reagent mixture solution. The holders configured for use with racks as described herein provide, in a self-contained manner, all of the reagents required to prepare a PCR-ready sample, or, when delivered to a user in kit form, contain in conjunction with other packages all of the required reagents. Suitable reagents, and protocols for using the same in DNA and RNA extractions can be found in, respectively, copending application Ser. Nos. 12/172,208, and 12/172,214, both filed Jul. 11, 2008 and incorporated herein by reference.

The racks herein are typically configured for use by an apparatus that carries out automated sample preparation, for example, on multiple samples simultaneously. An exemplary form of such an apparatus is further described herein, and can also be found described in U.S. provisional Patent Application Ser. No. 60/959,437, filed Jul. 13, 2007, incorporated herein by reference in its entirety, and in U.S. patent application Ser. No. 12/173,023, filed on Jul. 14, 2008 (and entitled "Integrated Apparatus for Performing Nucleic Acid Extraction and Diagnostic Testing on Multiple Biological Samples", in the name of Williams, et al.), incorporated by reference herein.

Rack

The racks herein are typically configured to be insertable, into, and removable from, a diagnostic or preparatory apparatus, each of the racks being further configured to receive a plurality of reagent holders, and to receive a plurality of sample tubes, wherein the reagent holders are in one-to-one correspondence with the sample tubes, and wherein the reagent holders each contain sufficient reagents to extract polynucleotides from a sample and place the polynucleotides into a PCR-ready form. Exemplary reagent holders are further described elsewhere herein and also in copending application Ser. No. 12/218,416, filed by ExpressMail on Jul. 14, 2008 (and entitled "Reagent Tube, Reagent Holder, and Kits Containing Same", in the name of Wilson, et al.) and incorporated herein by reference. An exemplary apparatus is outlined herein, and also described in U.S. patent application Ser. No. 12/173,023, filed on Jul. 14, 2008 (and entitled "Integrated Apparatus for Performing Nucleic Acid Extraction and Diagnostic Testing on Multiple Biological Samples", in the name of Williams, et al.), incorporated by reference herein.

Two perspective views of an exemplary rack 800, configured to accept 12 sample tubes and 12 corresponding reagent holders, in 12 lanes 850, are shown in FIG. 1. A lane 850, as used herein in the context of a rack, is a dedicated region of the rack designed to receive a sample tube and corresponding reagent holder. In the accompanying drawings, not all visible lanes are labeled; usually one lane or a pair of lanes in a given view is given reference number 850. Two perspective views of the same exemplary rack, in conjunction with a heater unit, as further described herein, are shown in FIG. 2.

A rack may accept 2, 4, 6, 8, 10, 12, 16, or 20 samples such as in sample tubes 802, and a corresponding number of holders 804. Thus the embodiment of FIG. 1 configured to receive 12 samples and 12 corresponding reagent holders is exemplary.

A rack is typically configured to accept a number of reagent holders 804, such as those further described herein, the rack being configured to hold one or more such holders, either permitting access on a laboratory benchtop to reagents stored in the holders, or situated in a dedicated region of the apparatus permitting the holders to be accessed by one or more other functions of the apparatus, such as automated pipetting, heating of the process tubes, and magnetic separating of affinity beads. Typically holders 804 each have at least one or more pipette tips, and one or more containers for reagents.

Figure 3:
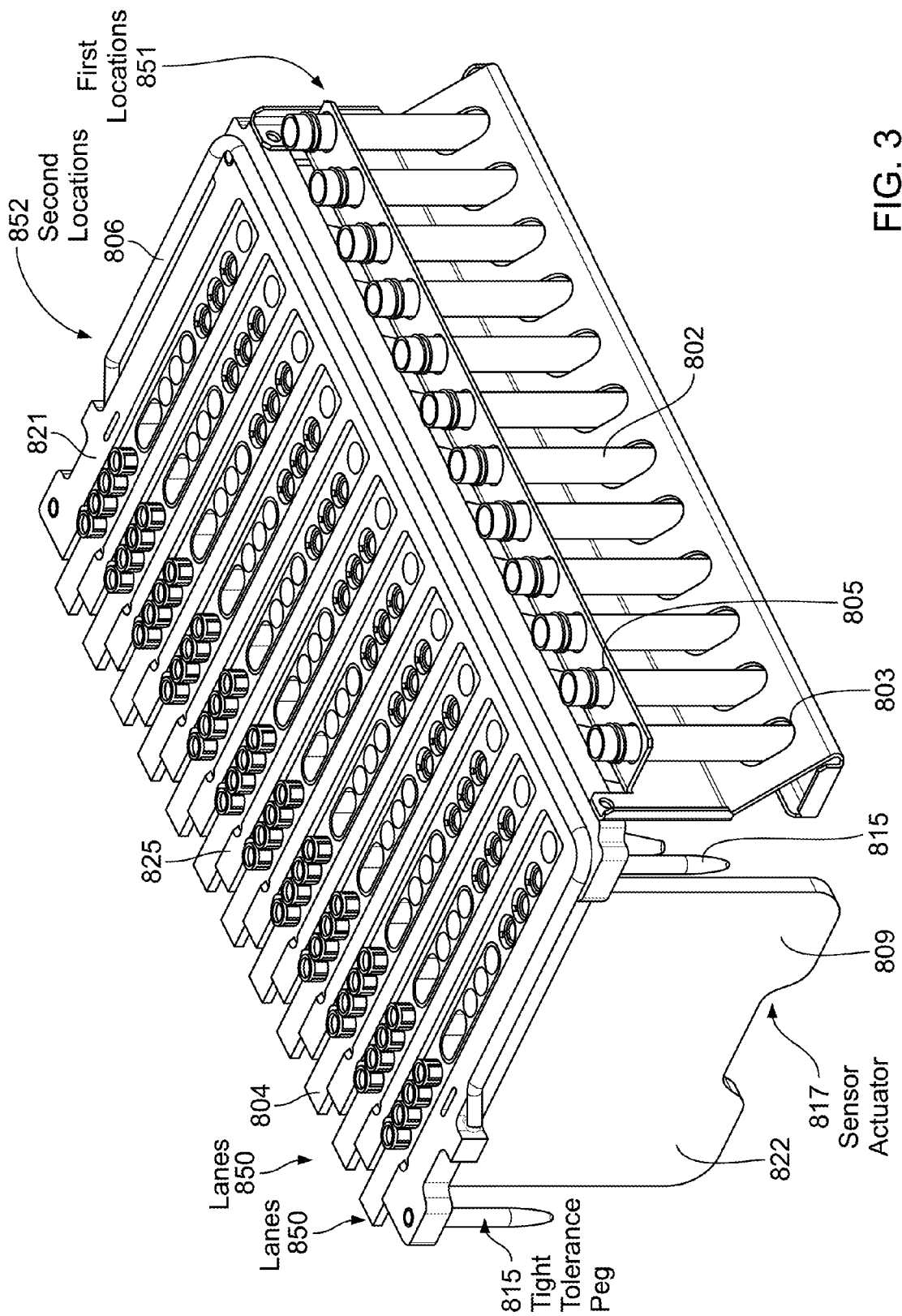
FIG. 3 shows a perspective view of an exemplary rack for samples and reagent holders.
Figure 4A:
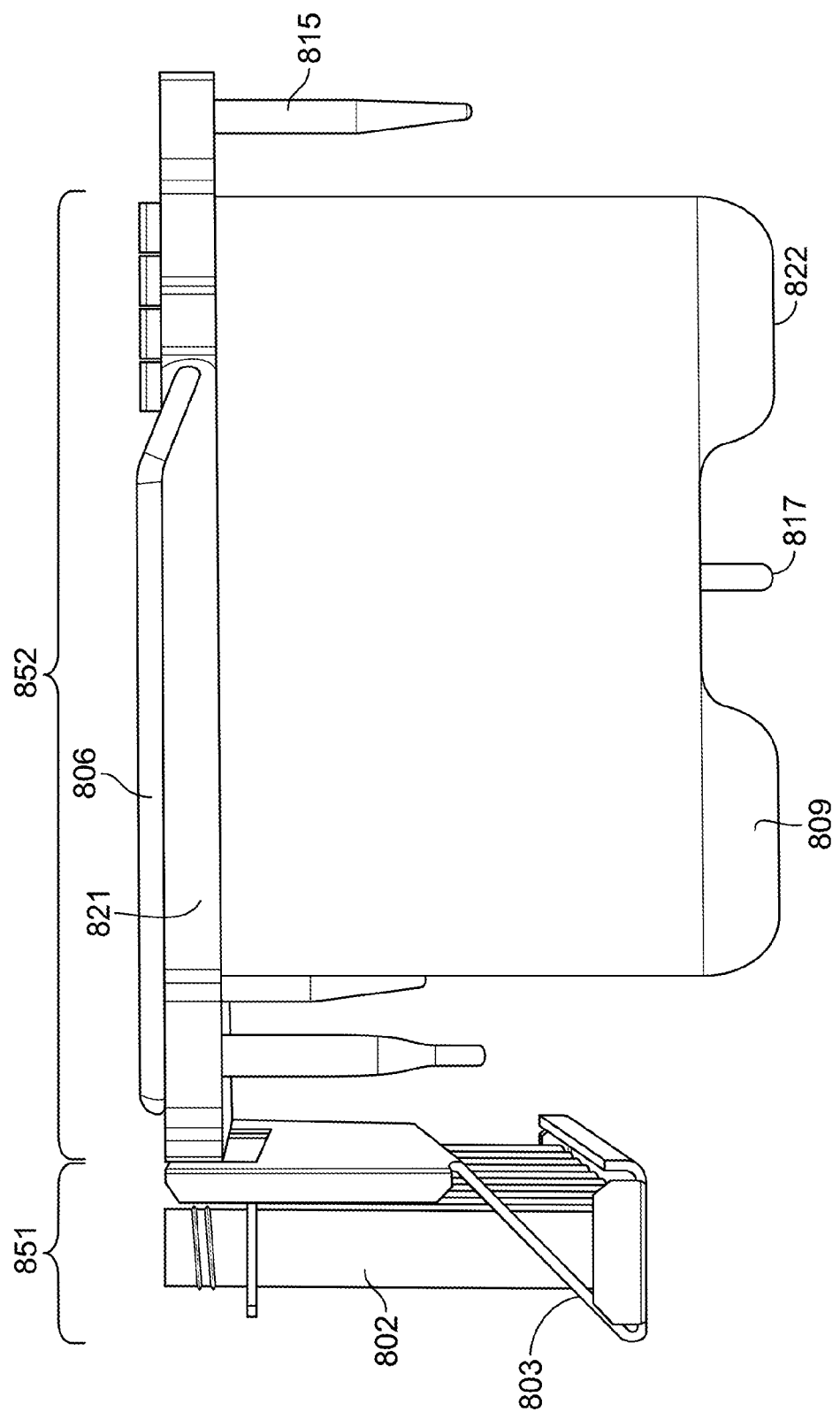
Figure 4B:
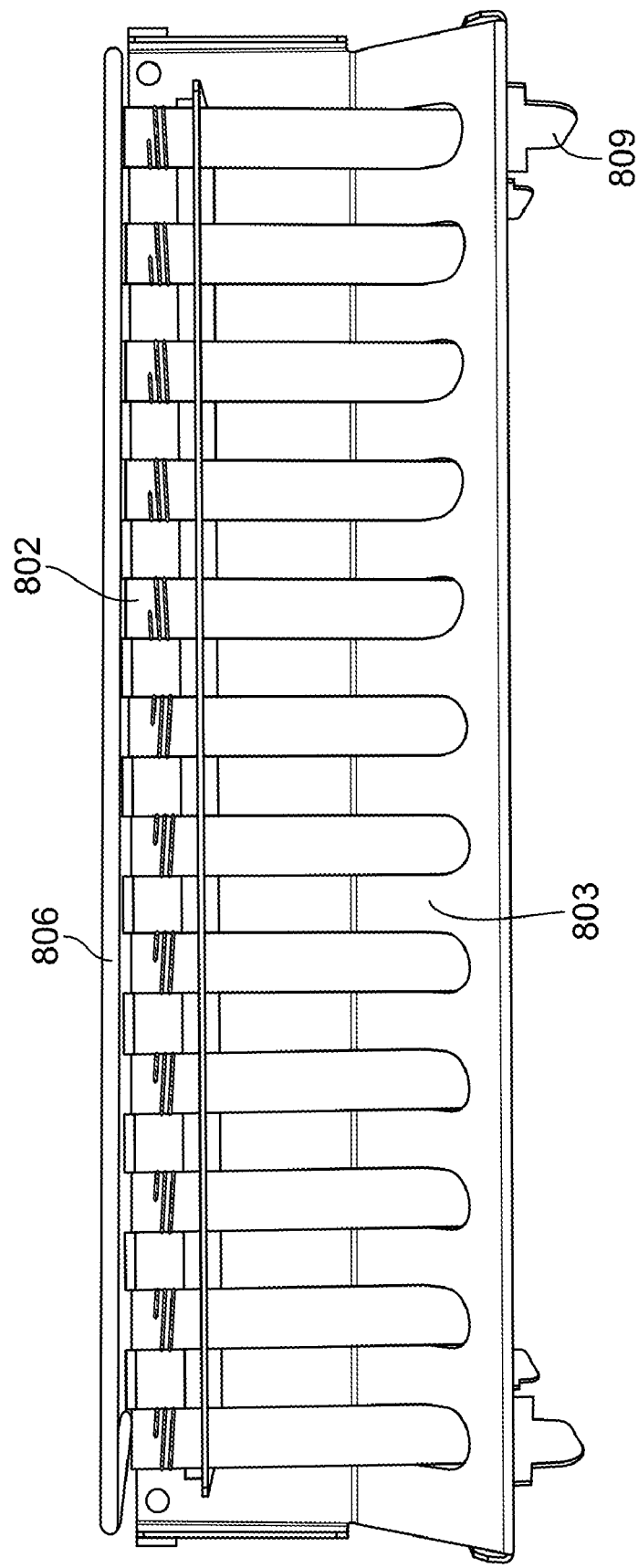
Figure 4C:
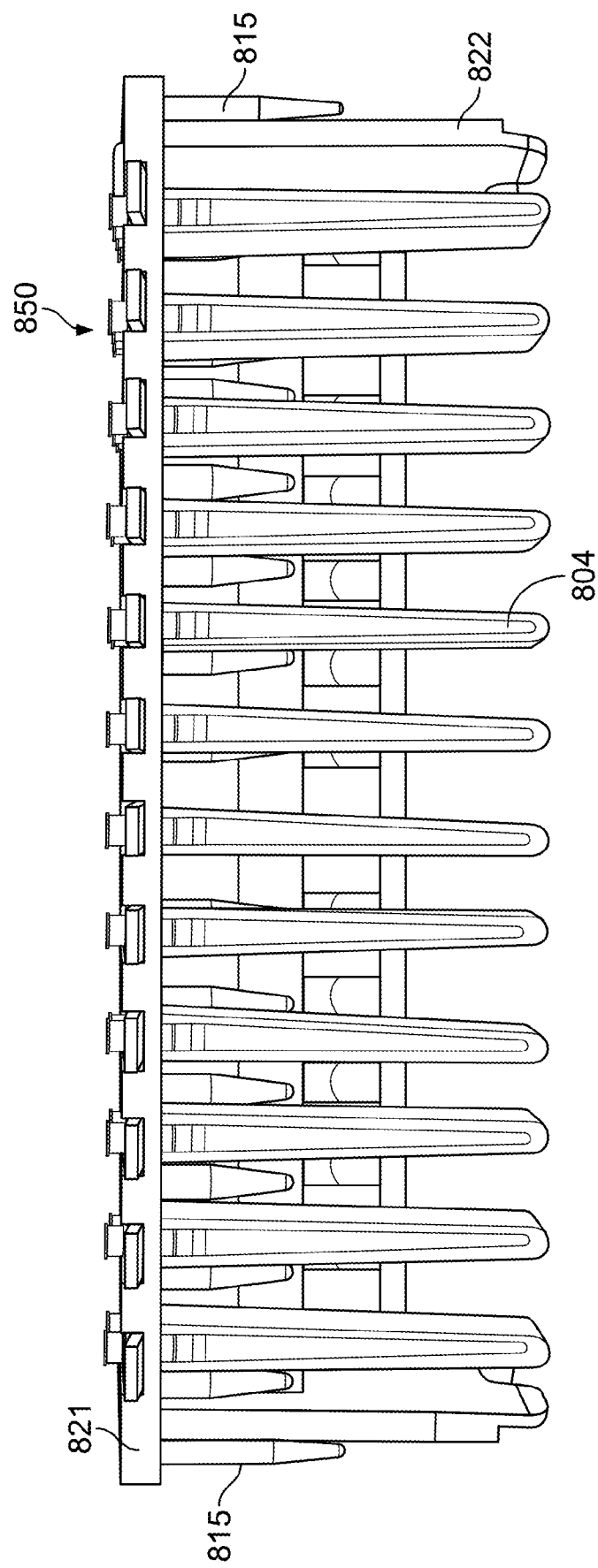
Figure 4D:
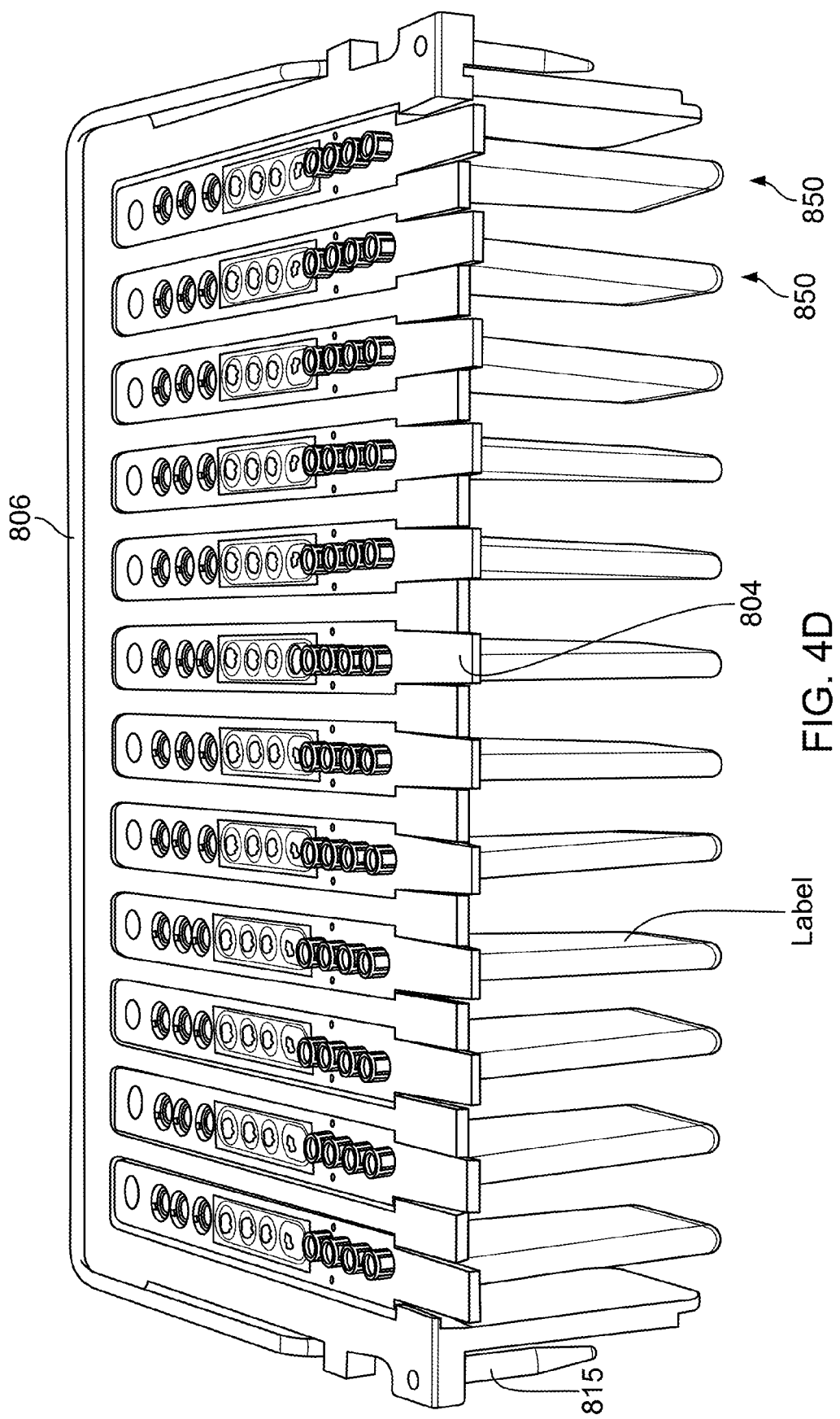
Figure 4E:
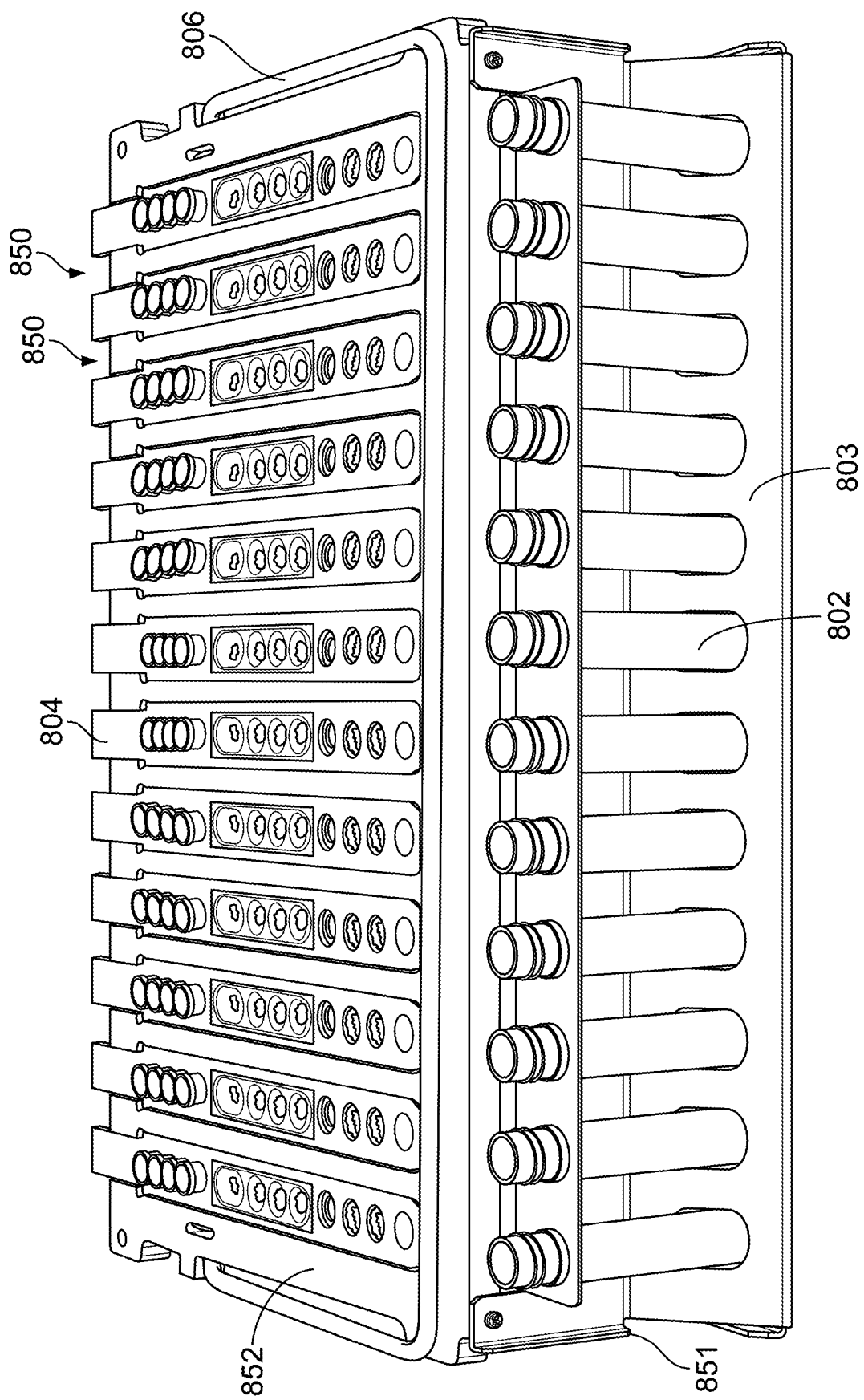
Figure 4F:
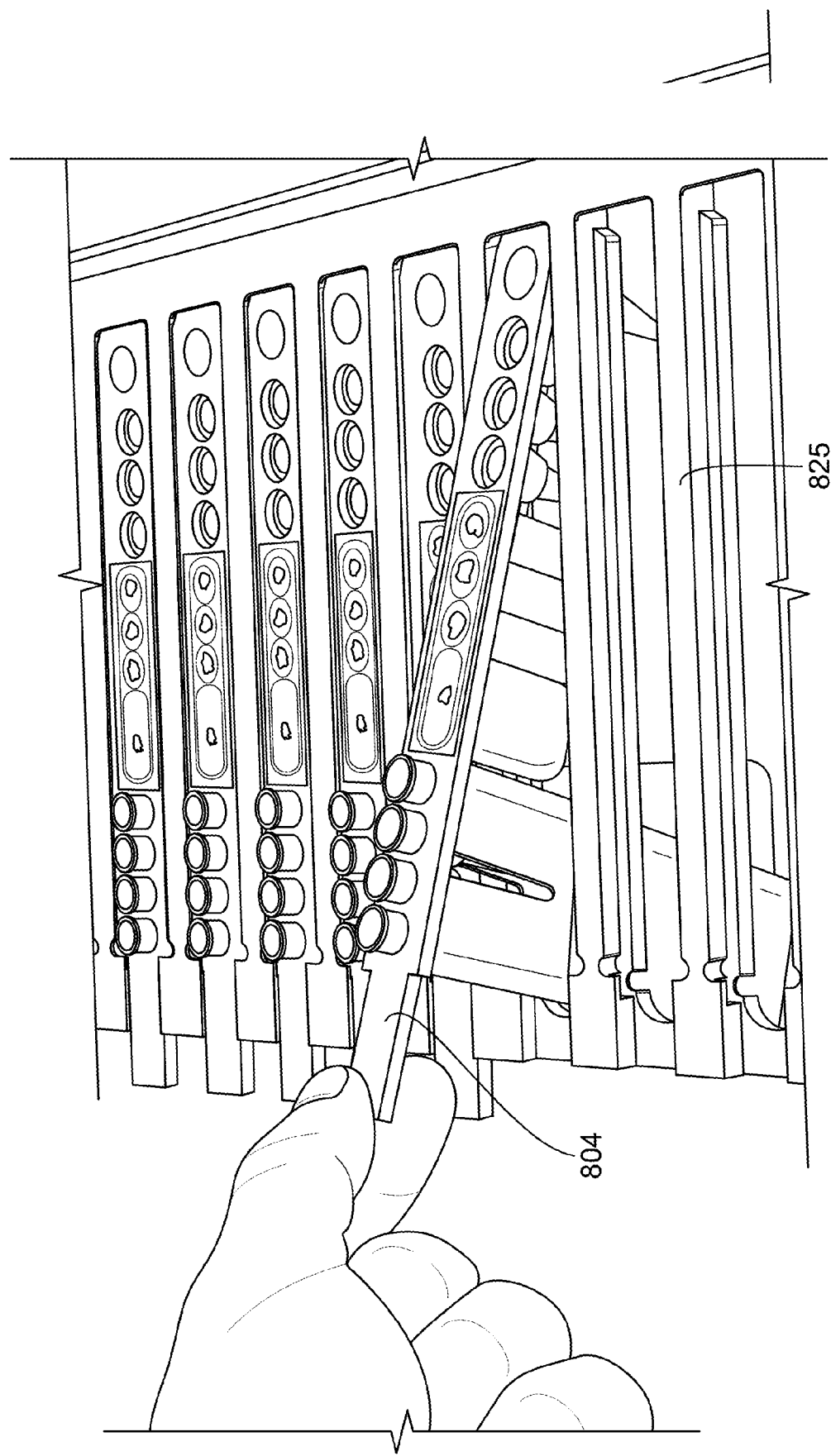
Figure 4G:
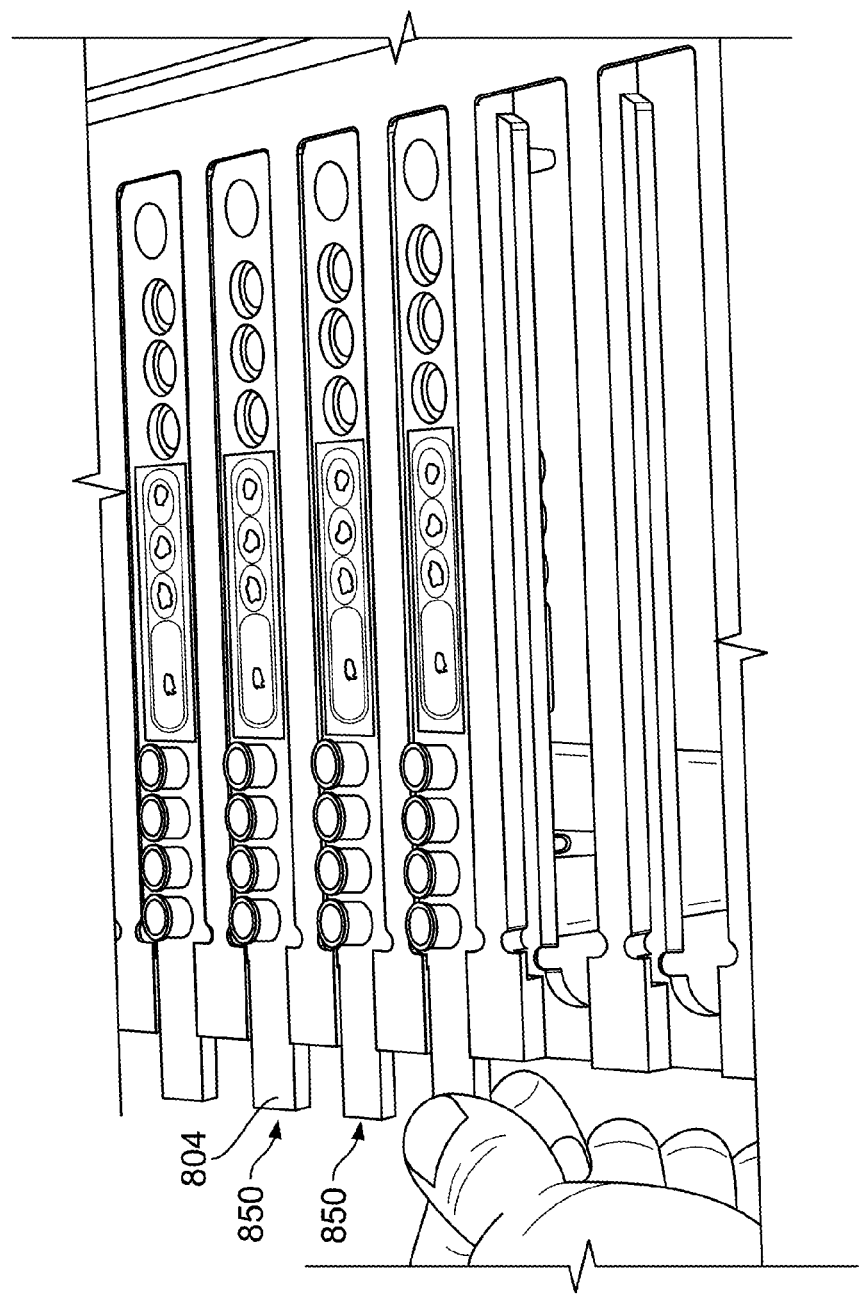
Figure 4H:
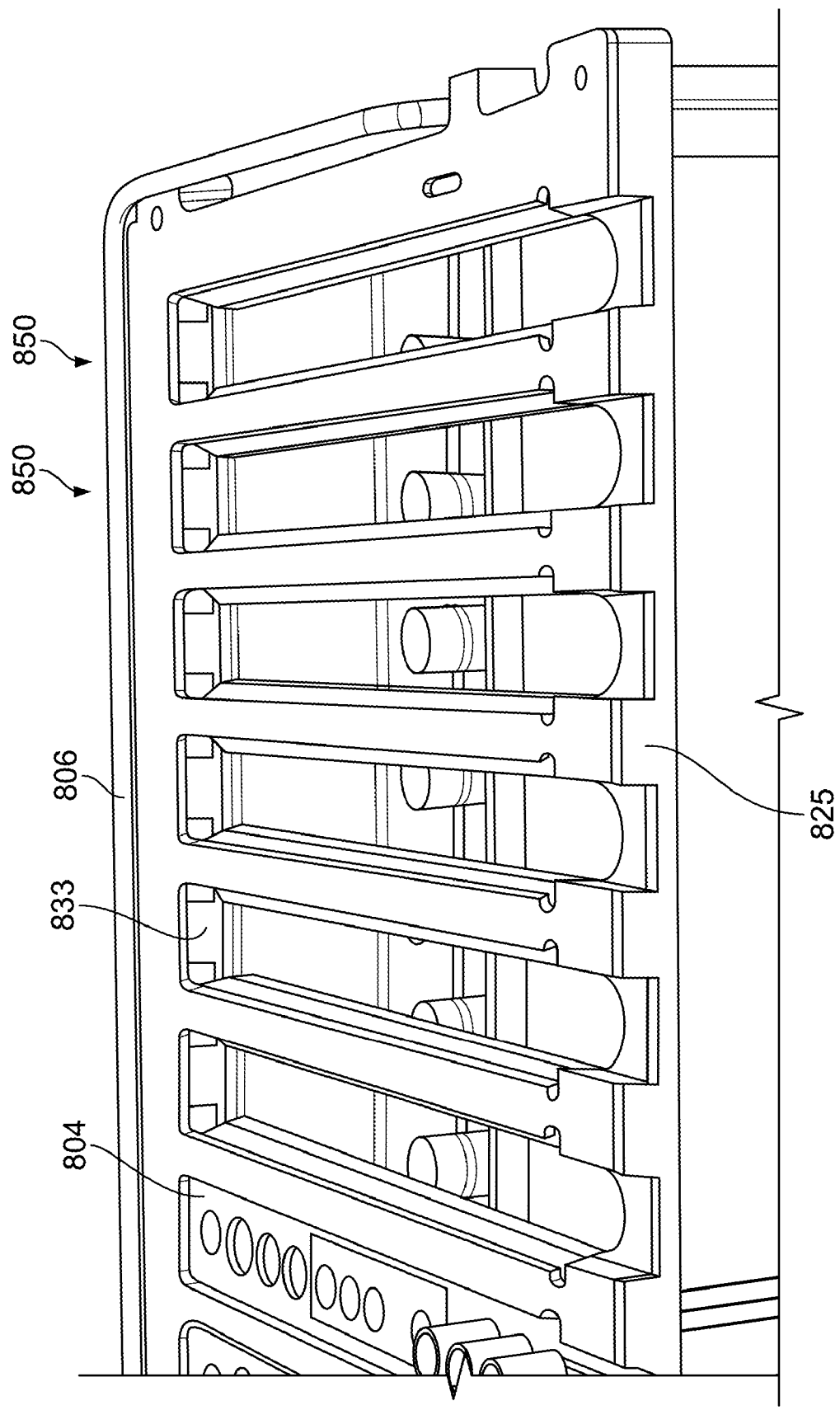
Figure 4I:
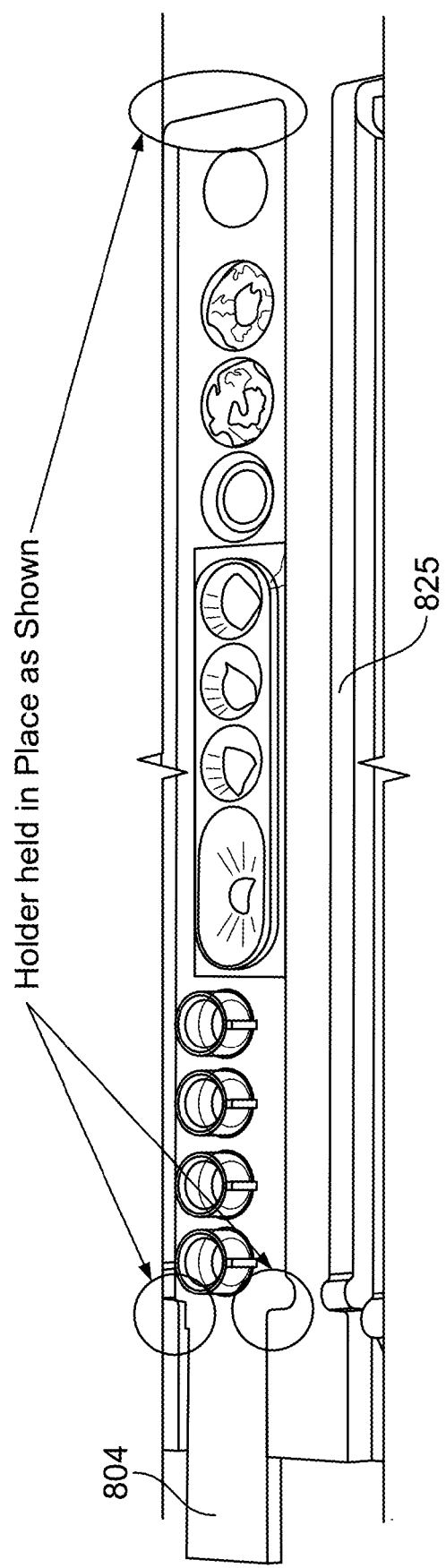
Figure 4K:
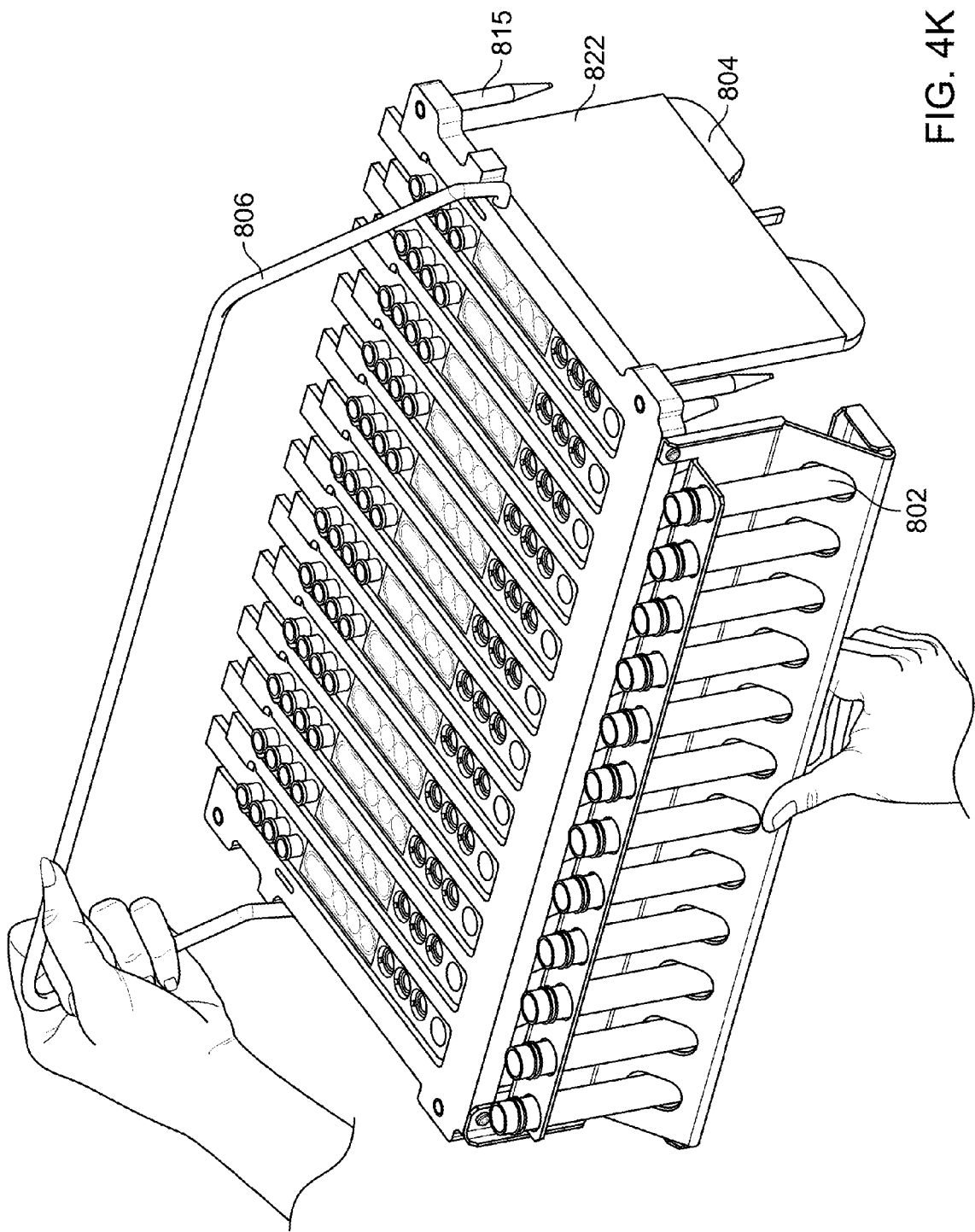

Various views of a second exemplary rack 800, also configured to accept 12 sample tubes and 12 reagent holders, are shown in FIG. 3, and FIGS. 4A-4K. Thus, the following views are shown: side plan (FIG. 4A); front plan, showing sample tubes (FIG. 4B); rear plan, showing reagent holders (FIG. 4C); rear elevation, showing reagent holders (FIG. 4D); front elevation, showing sample tubes (FIG. 4E); top, showing insertion of a reagent holder (FIGS. 4F and 4G); top showing slot for inserting a reagent holder (FIG. 4H); top view showing registration of reagent holder (FIG. 4I); close up of rack in state of partial insertion/removal from apparatus (FIG. 4J); and rack held by handle, removed from apparatus (FIG. 4K).

Figure 6:
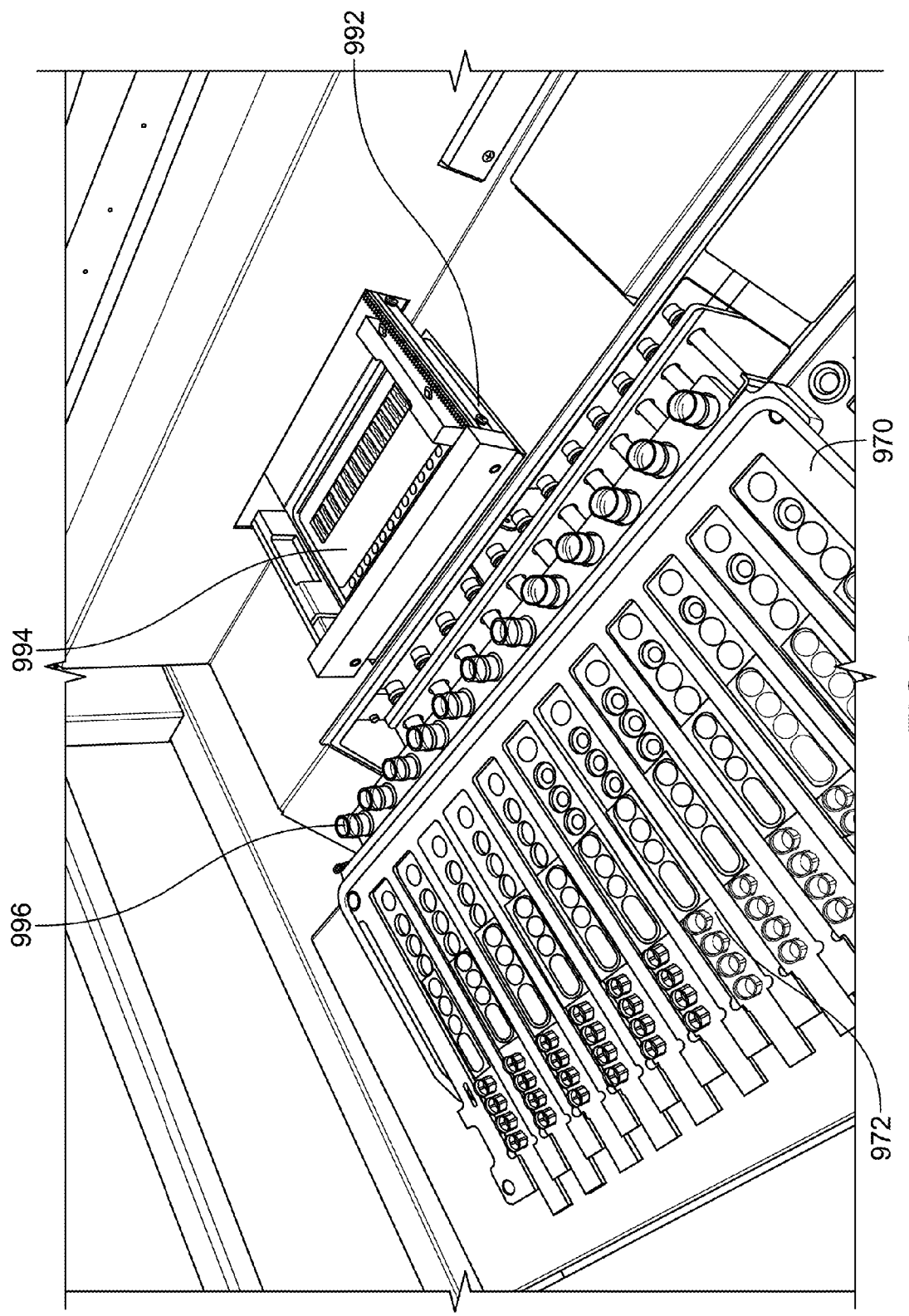
FIG. 6 shows a perspective view of an exemplary rack, carrying a number of sample tubes and reagent holders, and positioned in a diagnostic apparatus.

In FIG. 4J, two racks are visible: rack 800-1 is shown (in part) in position inserted fully into an apparatus 981; rack 800-2 is shown in a state of partial insertion or removal from apparatus 981. A recessed area, such as a receiving bay, in a diagnostic or preparatory apparatus 981, as further described herein, for accepting the exemplary removable rack of FIG. 3 is shown in FIG. 5. A rack, as shown in FIG. 3, situated in the recessed area of FIG. 5 is shown in FIG. 6, in location, in relation to a receiving bay 992 holding a microfluidic cartridge 994 that can be configured to carry out an amplification on a suitably prepared sample, as further described in U.S. patent application Ser. No. 12/173,023, filed on Jul. 14, 2008 (and entitled "Integrated Apparatus for Performing Nucleic Acid Extraction and Diagnostic Testing on Multiple Biological Samples", in the name of Williams, et al.). Other suitably configured recessed areas for receiving other racks differing in shape, appearance, and form, rather than function, are consistent with the description herein.

The two exemplary racks shown in FIGS. 1 and 3 being non-limiting, general features of racks contemplated herein are now described using the two exemplary racks as illustrative thereof. For example, in the embodiments shown here, at least the first lane and the second lane are parallel to one another, a configuration that increases pipetting efficiency. Typically, when parallel to one another, pairs of adjacent sample lanes 850 are separated by 24 mm at their respective midpoints. Other distances are possible, such as 18 mm apart, or 27 mm apart. The distance between the midpoints in dependent on the pitch of the nozzles in the liquid dispensing head, as further described herein. Keeping the spacing in multiples of 9 mm enables easy loading from the rack into a 96 well plate (where typically wells are spaced apart by 9 mm). Typically, also, the rack is such that the plurality of reagent holders in the plurality of lanes are maintained at the same height relative to one another.

The rack is configured to accept a given reagent holder in such a way that the reagent holder snaps or locks reversibly into place, and thereby remains steady while reagents are accessed in it, and while the rack is being carried from one place to another or is being inserted into, or removed from, a diagnostic apparatus.

In each embodiment of FIGS. 1 and 3, each of the second locations in the respective lanes comprises a mechanical key configured to accept the reagent holder in a single orientation. In FIG. 1, it is shown that the reagent holder(s) slide horizontally into vertically oriented slots, one per holder, located in the rack. In such an embodiment, the edge of a connecting member on the holder engages with a complementary groove in the upper portion of a slot. In FIGS. 4F, 4G, and 4I, it is shown that the reagent holder(s) can engage with the rack via a mechanical key that keeps the holders steady and in place. For example, the mechanical key can comprise a raised or recessed portion that, when engaging with a complementary portion of the reagent holder, permits the reagent holder to snap into the second location. It can also be seen in the embodiments shown that the reagent holder has a first end and a second end, and the mechanical key comprises a first feature configured to engage with the first end, and a second feature configured to engage with the second end in such a way that a reagent holder cannot be inserted into the rack the wrong way around. In some embodiments, as shown in FIG. 8H, a sprung metal tab 833 positioned inside the slot serves to keep the holder tightly in place against a stop at the opposite end of the slot.

In certain embodiments the reagent holders each lock into place in the rack, such as with a cam locking mechanism that is recognized as locked audibly and/or physically, or such as with a mechanical key.

The rack can be configured so that the holders, when positioned in it, are aligned for proper pipette tip pick-up using a liquid dispenser as further described herein. Furthermore, the second location of each lane can be deep enough to accommodate one or more pipette tips, such as contained in a pipette tip sheath.

In certain embodiments, the rack is configured to accept the samples in individual sample tubes 802, each mounted adjacent to a corresponding holder 804, for example on one side of rack 800. The sample tubes can be accessible to a sample identification verifier such as a bar code reader, as further described herein. In FIG. 1, a sample tube is held at its bottom by a cylindrical receiving member. In FIG. 3, it is shown that a sample tube can be held at both its top and bottom, such as by a recessed portion 803 configured to receive a bottom of a sample tube, and an aperture 805 configured to hold an upper portion of the sample tube. The aperture can be a ring or an open loop, or a hole in a metal sheet. The recessed portion can be as in FIG. 3, wherein it is an angled sheet of metal housing having a hole large enough to accommodate a sample tube. In alternate embodiments, a sample tube may be held at its lower portion by a member having an aperture and located above a base member on which the bottom of the sample tube rests.

The rack can be designed so that it can be easily removed from the apparatus and carried to and from the laboratory environment external to the apparatus, such as a bench, and the apparatus, for example, to permit easy loading of the sample tube(s) and the reagent holder(s) into the rack. In certain embodiments, the rack is designed to be stable on a horizontal surface, and not easily toppled over during carriage, and, to this end, the rack has one or more (such as 2, 3, 4, 6, 8) feet 809. In certain embodiments, the rack has a handle 806 to ease lifting and moving, and as shown in FIG. 1, the handle can be locked into a vertical position, during carriage, also to reduce risk of the rack being toppled over. The handle can optionally have a soft grip 808 in its middle. In the embodiment of FIG. 3, the carrying handle is positioned about an axis displaced from an axis passing through the center of gravity of the rack when loaded, and is free to fall to a position flush with an upper surface of the rack, under its own weight.

The embodiment of FIG. 1 has a metallic base member 810 having 4 feet 811 that also serve as position locators when inserting the rack into the dedicated portion of the apparatus. The handle is attached to the base member, but other attachments for a handle are possible. The portion of the rack 812 that accepts the samples and holders can be made of plastic, and comprises 12 slots, and may be disposable.

In the embodiment of FIG. 3, the rack comprises a housing, a plurality of lanes in the housing, and wherein each lane of the plurality of lanes comprises: a first location 851 configured to accept a sample tube; and a second location 852, configured to accept a reagent holder; and a registration member complementary to a receiving bay of a diagnostic apparatus. Typically, the housing is made of a metal, such as aluminum, that is both light but also can be machined to high tolerance and is sturdy enough to ensure that the rack remains stable when located in the diagnostic apparatus. The registration member in FIG. 3 comprises four (4) tight tolerance pegs 815, located one per corner of the rack. Such pegs are such that they fit snugly and tightly into complementary holes in a receiving area, such as a recessed area, of the apparatus and thereby stabilize the rack. Other embodiments having, for example, 2, or 3, or greater than 4 such pegs are consistent with the embodiments herein.

In particular, the housing in the embodiment of FIG. 3 comprises a horizontal member 821, and two or more vertical members 822 connected to the horizontal member, and is such that the second location 852 of each respective lane is a recessed portion within the horizontal member. The two or more vertical members 809 in the embodiment of FIG. 3 are configured to permit the rack to free stand thereon. The housing may further comprise two or more feet or runners, attached symmetrically to the first and second vertical members and giving the rack additional stability when positioned on a laboratory bench top.

Furthermore, in the embodiment of FIG. 3, the housing further comprises a plurality of spacer members 825, each of which is disposed between a pair of adjacent lanes. Optionally, such spacer members may be disposed vertically between the lanes.

Although not shown in the FIGs., a rack can further comprise a lane identifier associated with each lane. A lane identifier may be a permanent or temporary marking such as a unique number or letter, or can be an RFID, or bar-code, or may be a colored tag unique to a particular lane.

A rack is configured so that it can be easily placed at the appropriate location in a diagnostic apparatus and gives the user positive feedback, such as audibly or physically, that it is placed correctly. In certain embodiments, the rack can be locked into position. It is desirable that the rack be positioned correctly, and not permitted to move thereafter, so that movement of the liquid dispenser will not be compromised during liquid handling operations. The rack therefore has a registration member to ensure proper positioning. In the embodiment of FIG. 3, the registration member comprises two or more positioning pins configured to ensure that the rack can only be placed in the diagnostic apparatus in a single orientation; and provide stability for the rack when placed in the diagnostic apparatus. The embodiment of FIG. 3 has, optionally, a sensor actuator 817 configured to indicate proper placement of the rack in the diagnostic apparatus. Such a sensor may communicate with a processor 980 to provide the user with a warning, such as an audible warning, or a visual warning communicated via an interface, if the rack is not seated correctly. It may also be configured to prevent a sample preparation process from initiating or continuing if a seating error is detected.

In certain embodiments, the interior of the rack around the location of process tubes in the various holders is configured to have clearance for a heater assembly and/or a magnetic separator as further described herein. For example, the rack is configured so that process chambers on the individual holders are accepted by heater units in a heater assembly as further described herein.

Having a removable rack enables a user to keep a next rack loaded with samples and in line while a previous rack of samples is being processed by the apparatus, so that thereby the apparatus usage time and throughput is maximized.

The rack can also be conveniently cleaned outside of the instrument in case of any sample or reagent spills over it or just as a routine maintenance of laboratory wares.

In certain embodiments the racks have one or more disposable parts.

Reagent Holders

Described herein are reagent holders for holding and transporting reagents for various purposes, in particular sample preparation in a clinical context, and configured to be received by a rack as described herein. The reagent holders also typically provide a container in which various reagents can be mixed one with another and/or with a sample. The reagent holders typically permit snapping in of one or more tubes of analyte specific reagents (ASR's) and/or sample preparation reagents, and carrying out liquid dispensing processes, associated with sample preparation, that minimize cross-sample contamination but permit multiple PCR preparations to be performed from a single clinical sample. The holders are also configured for use in an automated preparatory apparatus that can carry out sample preparation on samples in more than one holder simultaneously.

Figure 7A:
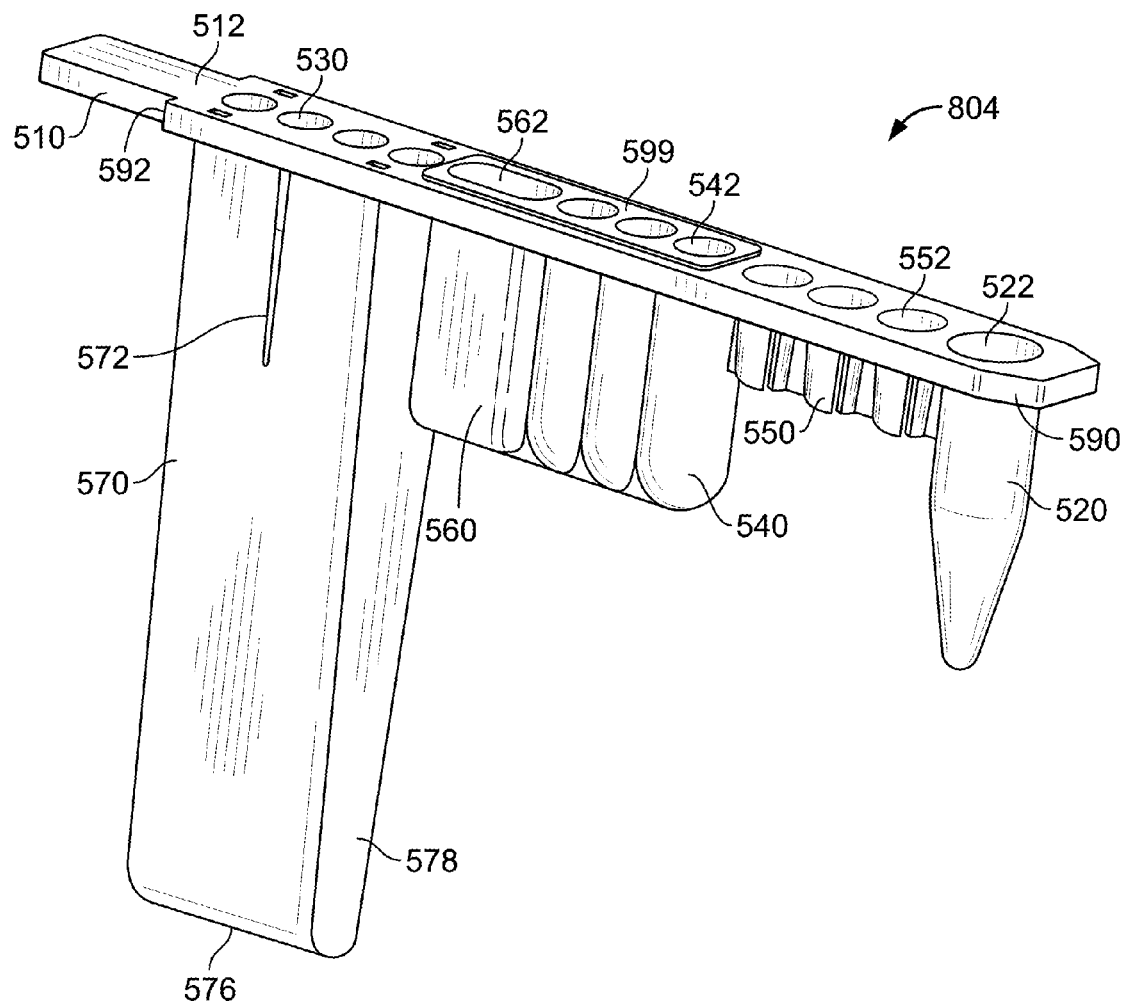
FIGS. 7A and 7B show an exemplary embodiment of a reagent holder having a pipette sheath, in perspective view (FIG. 7A) and underside view (FIG. 7B).
Figure 7B:
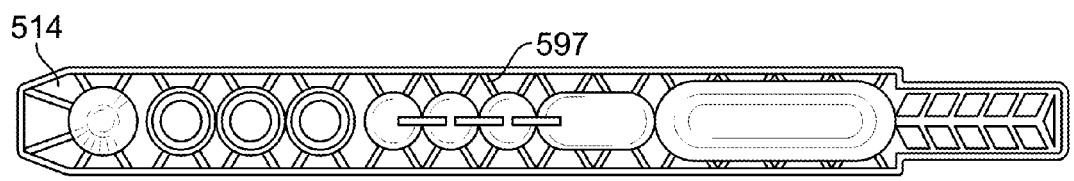

FIGS. 7A and 7B show views of an exemplary holder 804 as further described herein. This exemplary holder, as well as others consistent with the written description herein though not shown as specific embodiments, are now described.

The exemplary holder shown in FIGS. 7A and 7B can also be referred to as a "unitized disposable strip", or a "unitized strip", because it is intended to be used as a single unit that is configured to hold all of the reagents and receptacles necessary to perform a sample preparation, and because it is laid out in a strip format. It is consistent with the description herein, though, that other geometric arrangements of the various receptacles of the holder are contemplated, so that the description is not limited to a linear, or strip, arrangement, but can include a circular or grid arrangement. Accordingly, a rack as described herein can alternatively be configured to accept reagent holders that adopt other shapes than strips. Alternative shapes could be square, rectangular, and circular.

The exemplary holder of FIG. 7A comprises a connecting member 510 having one or more characteristics as follows. Connecting member 510 serves to connect various components of the holder together. Connecting member 510 has an upper side 512 and, opposed to the upper side, an underside 514.

The reagent holder of FIG. 7A is configured to comprise: a process tube 520 affixed to the connecting member and having an aperture 522 located in the connecting member; at least one socket 530, located in the connecting member, the socket configured to accept a disposable pipette tip 580; an optional pipette sheath 570 as further described herein; two or more reagent tubes 540 disposed on the underside of the connecting member, each of the reagent tubes having an inlet aperture 542 located in the connecting member; and one or more receptacles 550, located in the connecting member, wherein the one or more receptacles are each configured to receive a complementary container such as a reagent tube (not shown) inserted from the upper side 512 of the connecting member. The lanes of the rack described herein are designed to have sufficient depth and width to accommodate the various reagent tubes, receptacles, process tube, and pipette sheath of a given reagent holder.

In FIG. 7B, a view of underside 514 is shown, having various struts 597 connecting a rim of the connecting member with variously the sockets, process tube, and reagent tubes. Struts 597 are optional, and may be omitted all or in part, or may be substituted by, in all or in part, other supporting pieces that connect various parts of the holder to one another.

The one or more receptacles 550 are configured to accept reagent tubes that contain, respectively, sufficient quantities of one or more reagents typically in solid form, such as in lyophilized form, for carrying out extraction of nucleic acids from a sample that is associated with the holder. The receptacles can be all of the same size and shape, or may be of different sizes and shapes from one another. Receptacles 550 are shown as having open bottoms, but are not limited to such topologies, and may be closed other than the inlet 552 in the upper side of connecting member 510. Preferably the receptacles 550 are configured to accept commonly used containers in the field of laboratory analysis, or containers suitably configured for use with the holder herein. The containers are typically stored separately from the holders to facilitate sample handling, since solid reagents normally require different storage conditions from liquid reagents. In particular many solid reagents may be extremely moisture sensitive.

The snapped-in reagent tubes containing different reagents may be of different colors, or color-coded for easy identification by the user. For example they may be made of different color material, such as tinted plastic, or may have some kind of identifying tag on them, such as a color stripe or dot. They may also have a label printed on the side, and/or may have an identifier such as a barcode on a sealing layer on their respective tops.

The containers 554 received by the receptacles 550 may alternatively be an integrated part of the holder and may be the same type of container as the waste chamber and/or the reagent tube(s), or may be different therefrom.

In one embodiment, the containers 554 containing lyophilized reagents, disposed in the receptacles 550, are 0.3 ml tubes that have been further configured to have a star-shaped pattern on their respective bottom interior surfaces. This is so that when a fluid has been added to the lyophilized reagents (which are dry in the initial package), a pipette tip can be bottomed out in the tube and still be able to withdraw almost the entire fluid from the tube. The design of the star-pattern is further described elsewhere in U.S. patent application Ser. No. 12/178,557, filed on even date herewith, and entitled "Reagent Tube", in the name of Handique et al., which application is incorporated herein by reference.

The embodiment of a reagent holder 804 is shown configured with a waste chamber 560, having an inlet aperture 562 in the upper side of the connecting member. Waste chamber 560 is optional and, in embodiments where it is present, is configured to receive spent liquid reagents. In other embodiments, where it is not present, spent liquid reagents can be transferred to and disposed of at a location outside of the holder, such as, for example, a sample tube that contained the original sample whose contents are being analyzed. Waste chamber 560 is shown as part of an assembly comprising additionally two or more reagent tubes 540. It would be understood that such an arrangement is done for convenience, e.g., of manufacture; other locations of the waste chamber are possible, as are embodiments in which the waste chamber is adjacent a reagent tube, but not connected to it other than via the connecting member.

The embodiment of a reagent holder 804 is shown having a pipette sheath 570. This is an optional component of the holders described herein. It may be permanently or removably affixed to connecting member 510, or may be formed, e.g., moulded, as a part of a single piece assembly for the holder. Pipette sheath 570 is typically configured to surround the at least one socket and a tip and lower portion of a pipette tip when the pipette tip is stationed in the at least one socket. In some embodiments, the at least one socket comprises four sockets. In some embodiments the at least one socket comprises two, three, five, or six sockets.

Pipette sheath 570 typically is configured to have a bottom 576 and a walled portion 578 disposed between the bottom and the connecting member. Pipette sheath 570 may additionally and optionally have one or more cut-out portions 572 in the wall 578, or in the bottom 576. Such cutouts provide ventilation for the pipette tips and also reduce the total amount of material used in manufacture of the holder, and may have various numbers, positions, shapes and sizes, as further described in U.S. patent application Ser. No. 12/218, 416, filed by ExpressMail on Jul. 14, 2008, entitled "Reagent Tube, Reagent Holder, and Kits Containing Same", in the name of Wilson, et al., and incorporated herein by reference.

In embodiments having a pipette sheath, a purpose of the sheath is to catch drips from used pipette tips, and thereby to prevent cross-sample contamination, from use of one holder to another in a similar location, and/or to any supporting rack in which the holder is situated. Typically, then, the bottom 576 is solid and bowl-shaped (concave) so that drips are retained within it. An embodiment having no pipette sheath, could utilize, e.g., a drip tray or a drainage outlet, suitably placed beneath pipette tips located in the one or more sockets, for the same purpose and located under or in the bottom of the rack, as described herein. In addition to catching drips, the pipette tip sheath prevents or inhibits the tips of other reagent holders—such as those that are situated adjacent to the one in question in a rack as further described herein—from touching each other when the tips are picked up and/or dropped off before or after some liquid processing step. Contact between tips in adjacent holders is generally not intended by, for example, an automated dispensing head that controls sample processing on holders in parallel, but the pipette tips being long can easily touch a tip in a nearby holder if the angle when dropping off of the tip deviates slightly from vertical.

Process tube 520 can also be a snap-in tube, rather than being part of an integrated piece. Process tube 520 is typically used for various mixing and reacting processes that occur during sample preparation. For example, cell lysis can occur in process tube 520, as can extraction of nucleic acids, such as DNA or RNA of a patient, and DNA or RNA of a pathogen. Process tube 520 is then advantageously positioned in a location that minimizes, overall, pipette head moving operations involved with transferring liquids to process tube 520. Process tube 520 is also located in the holder in such a position that, when the holder is inserted in a rack as further described herein, the process tube is exposed and accessible to a heater and separator, as further described herein.

Some of the reagents contained in the holder are provided as liquids, and others may be provided as solids. In some embodiments, a different type of container or tube is used to store liquids from those that store the solids.

Reagent tubes 540 are typically configured to hold liquid reagents, one per tube. For example, in reagent holder embodiment 804, three reagent tubes are shown, containing respectively wash buffer, release buffer, and neutralization buffer, each of which is used in a sample preparation protocol.

Reagent tubes 540 that hold liquids or liquid reagents can be sealed with a laminate structure 598 to facilitate long term storage. The laminate structure typically has a heat seal layer, a plastic layer such as a layer of polypropylene, and a layer of metal such as aluminum foil, wherein the heat seal layer is adjacent the one or more reagent tubes. The additional plastic film that is used in a laminate for receptacles that contain liquid reagents is typically to prevent liquid from contacting the aluminum. Various embodiments of a laminate structure are described in U.S. patent application Ser. No. 12/218,416, filed by ExpressMail on Jul. 14, 2008, entitled "Reagent Tube, Reagent Holder, and Kits Containing Same", in the name of Wilson, et al., and incorporated herein by reference. In some embodiments, a raised flat portion 599 facilitates application and removal of laminate 598. Raised surface 599, on the upper side of the connecting member, and surrounding the inlet apertures to the reagent tubes and, optionally, the waste chamber, is an optional feature of the holder.

The containers that hold solid, such as lyophilized reagents, can be sealed across their tops by a metal foil, such as an aluminum foil, with no plastic lining layer, as further described herein.

The reagent holder 804 has a connecting member that is configured so that the at least one socket, the one or more receptacles, and the respective apertures of the process tube, and the two or more reagent tubes, are all arranged linearly with respect to one another (i.e., their midpoints lie on the same axis). However, the holders herein are not limited to particular configurations of receptacles, process tube, sockets, reagent tubes, and waste chamber if present. For example, a holder may be made shorter, if some apertures are staggered with respect to one another and occupy 'off-axis' positions. The various receptacles, etc., also do not need to occupy positions with respect to one another that are the same as those shown in FIGS. 7A and 7B. Thus, in FIGS. 7A, and 7B, the process tube is on one end of the connecting member, and the pipette sheath is at the other end, adjacent to, in an interior position, a waste chamber and two or more reagent tubes. Still other dispositions are possible, such as mounting the process tube on one end of the holder, mounting the process tube adjacent the pipette tips and pipette tip sheath (as further described herein), and mounting the waste tube adjacent the process tube. It would be understood that alternative configurations of the various parts of the holder give rise only to variations of form and can be accommodated within other variations of the apparatus as described, including but not limited to alternative instruction sets for a liquid dispensing pipette head, heater assembly, and magnetic separator, as further described herein. Each such configuration of the reagent holder can be accommodated by a corresponding variation in form of the rack described herein that receives one or more such holders.

The materials of the various tubes and chambers may be configured to have at least an interior surface smoothness and surface coating to reduce binding of DNA and other macromolecules thereto. Binding of DNA is unwanted because of the reduced sensitivity that is likely to result in subsequent detection and analysis of the DNA that is not trapped on the surface of the holder.

The process tube also may have a low binding surface, and allows magnetic beads to slide up and down the inside wall easily without sticking to it. Moreover, it has a hydrophobic surface coating enabling low stiction of fluid and hence low binding of nucleic acids and other molecules.

In some embodiments, the holder comprises a registration member such as a mechanical key. Typically such a key is part of the connecting member 510. A mechanical key ensures that the holder is accepted by a complementary member in, for example, a supporting rack as described herein or a receiving bay of an apparatus that controls pipetting operations on reagents in the holder. A mechanical key is normally a particular-shaped cut-out that matches a corresponding cutout or protrusion in a rack or receiving apparatus. Thus, embodiment 804 has a mechanical key 592 that comprises a pair of rectangular-shaped cut-outs on one end of the connecting member. This feature as shown additionally provides for a tab by which a user may gain a suitable purchase when inserting and removing the holder into a rack or another apparatus. Embodiment 804 also has a mechanical key 590 at the other end of connecting member 510. Key 590 is an angled cutout that eases insertion of the holder into a rack, as well as ensures a good registration therein when abutting a complementary angled cut out in a recessed area configured to receive the holder. Other variations of a mechanical key are, of course, consistent with the description herein: for example, curved cutouts, or various combinations of notches or protrusions all would facilitate secure registration of the holder.

In some embodiments, not shown in FIGS. 7A, 7B, the holder further comprises an identifier affixed to the connecting member. The identifier may be a label, such as a writable label, a bar-code, a 2-dimensional bar-code, or an RFID tag. The identifier can be, e.g., for the purpose of revealing quickly what combination of reagents is present in the holder and, thus, for what type of sample preparation protocol it is intended. The identifier may also indicate the batch from which the holder was made, for quality control or record-keeping purposes. The identifier may also permit a user to match a particular holder with a particular sample.

It should also be considered consistent with the description herein that a holder additionally can be configured to accept a sample, such as in a sample tube. Thus, in embodiments described elsewhere herein, a rack accepts a number of sample tubes and a number of corresponding holders in such a manner that the sample tubes and holders can be separately and independently loaded from one another. Nevertheless, in other embodiments, a holder can be configured to also accept a sample, for example in a sample tube. And thus, a complementary rack is configured to accept a number of holders, wherein each holder has a sample as well as reagents and other items. In such an embodiment, the holder is configured so that the sample is accessible to a sample identification verifier.

A reagent holder for use with a rack as described herein is typically made of a plastic such as polypropylene. The plastic is such that it has some flexibility to facilitate placement into a rack, as further described herein. The plastic is typically sufficiently rigid, however, so that the holder will not significantly sag or flex under its own weight and will not easily deform during routine handling and transport, and thus will not permit reagents to leak out from it.

The holder is typically such that the connecting member, process tube, the two or more reagent tubes, and the waste chamber (if present) are made from a single piece, made from a material such as polypropylene.

The reagent holder for use herein is also typically such that at least the process tube, and the two or more reagent tubes are translucent.

The reagent holders can be disposable, such as intended for a single use, following which it is discarded.

Liquid Dispenser

Additionally, the holders herein are configured, when received by a rack as described elsewhere herein, to accept pipette operations both performed manually by an operator, and by an automated pipette head. An exemplary automated pipette head is described in U.S. provisional application Ser. No. 60/959,437, filed Jul. 13, 2008, and in U.S. patent application Ser. No. 12/173,023, filed Jul. 14, 2008, entitled "Integrated Apparatus for Performing Nucleic Acid Extraction and Diagnostic Testing on Multiple Biological Samples", in the name of Williams, et al., both of which are incorporated herein by reference in their entirety. Typical features of an automated pipette head suitable for operating with holders as described herein include at least: an ability to pick up pipette tips from the one or more sockets, and to return pipette tips to such sockets after use; to strip and discard a pipette tip from a pipette head after use or upon encountering an error; move a pipette tip with precision from one location of a given holder to another so that, for example, liquid reagents can be located and added to solid reagents to make up solutions, and various liquid reagents can be mixed with one another during a sample preparation protocol. Furthermore, it is desirable that such an automated pipette device can operate on several, such as 2, 3, 4, or 6, holders simultaneously when received by a rack, and thereby perform certain operations in parallel. Thus the pipette head should move in three degrees of freedom.

Heater Assembly & Magnetic Separator

The racks as described herein are configured such that reagent holders are positioned so that the process tube is heated by a dedicated heating unit 977, for example situated in an apparatus for carrying out sample preparation on multiple samples in parallel, as shown in FIG. 2. Typically such a heater assembly comprises one or more independently controllable heater units 1010, each of which comprises a heat block configured to heat a process tube in a reagent holder situated in the rack, as further described herein. In one embodiment, a heat element is a power resistor. The right hand panel of FIG. 2 shows how holders loaded in a rack can be positioned in close proximity to a dedicated heating unit. The heating unit is configured to heat the process tube in each of one or more reagent holders positioned in the rack, without unduly heating other portions of the rack, or other containers associated with the reagent holders.

Yet additionally, the holders herein are configured so that the process tube is in close enough proximity to a magnetic assembly that separation of magnetic particles from reagents in solution in the process tube can be accomplished. An exemplary magnetic separator is configured to move one or more magnets relative to the one or more process tubes. Typically, the magnet is mounted in such a way that it can be moved in proximity to the process tubes, either in an automated fashion such as under control of a processor, or manually. The magnet can be made of neodymium (e.g., from K & J Magnetics, Inc.) and can have a magnetic strength of 5,000-15,000 Gauss (Brmax). The poles of the magnets can be arranged such that one pole faces the heat blocks and the other faces away from the heat blocks.

Advantageously, the heater assembly and magnetic separator operate together to permit successive heating and separation operations to be performed on liquid materials in the one or more process tubes without transporting either the liquid materials or the process tubes to different locations to perform either heating or separation. An exemplary heater assembly and magnetic separator are further described in U.S. provisional Patent Application Ser. No. 60/959,437, filed Jul. 13, 2008, and U.S. patent application Ser. No. 12/173,023, filed Jul. 14, 2008, entitled "Integrated Apparatus for Performing Nucleic Acid Extraction and Diagnostic Testing on Multiple Biological Samples", in the name of Williams, et al., and "Ser. No. 12/178,586, entitled "Integrated Heater and Magnetic Separator", in the name of Handique, filed on even date herewith, all of which are incorporated herein by reference in their entirety.

Apparatus Overview

Figure 8:
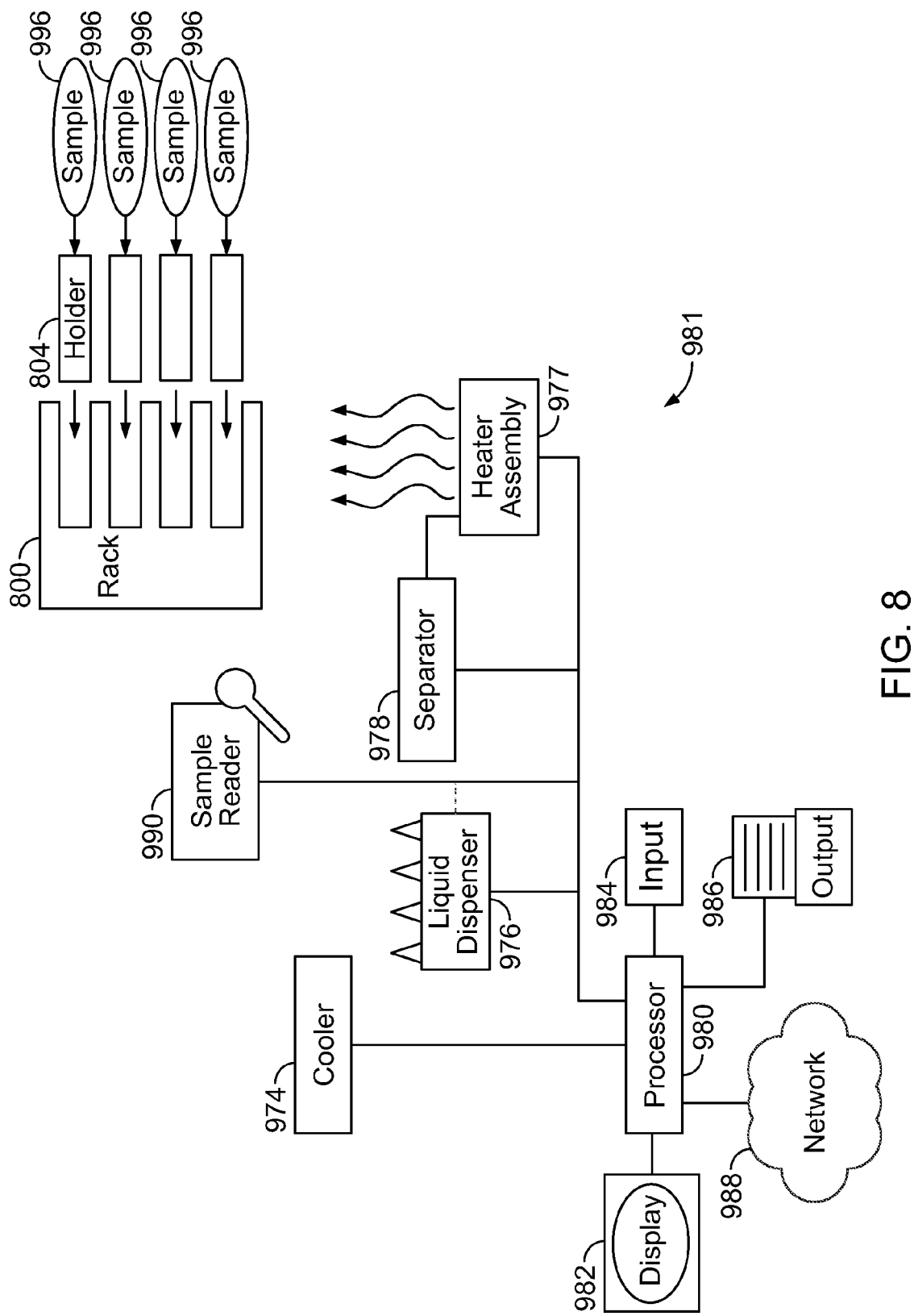
FIG. 8 shows a schematic of an automated apparatus configured to carry out sample preparation using a rack as described herein.

A schematic overview of an apparatus 981 for carrying out automated sample preparation on multiple samples in parallel, according to steps exemplified elsewhere herein, is shown in FIG. 8. The geometric arrangement of the components of system 981 is schematic and not intended to be limiting. The apparatus may additionally comprise (not shown in FIG. 8) a microfluidic cartridge, in a receiving bay, and configured to carry out a diagnostic test on the sample, such as by detecting presence of an amplified polynucleotide in the cartridge. Such additional features are also described in U.S. patent application Ser. No. 12/173,023, filed on Jul. 14, 2008 (and entitled "Integrated Apparatus for Performing Nucleic Acid Extraction and Diagnostic Testing on Multiple Biological Samples", in the name of Williams, et al.).

A processor 980, such as a microprocessor, is configured to control functions of various components of the system as shown, and is thereby in communication with each such component requiring control. It is to be understood that many such control functions can optionally be carried out manually, and not under control of the processor. Furthermore, the order in which the various functions are described, in the following, is not limiting upon the order in which the processor executes instructions when the apparatus is operating. Thus, processor 980 can be configured to receive data about a sample to be analyzed, e.g., from a sample reader 990, which may be a barcode reader, an optical character reader, or an RFID scanner (radio frequency tag reader).

Processor 980 can be configured to accept user instructions from an input device 984, where such instructions may include instructions to start analyzing the sample, and choices of operating conditions. Processor 980 can be also configured to communicate with a display 982, so that, for example, information about an analysis is transmitted to the display and thereby communicated to a user of the system. Such information includes but is not limited to: the current status of the apparatus; progress of PCR thermocycling; and a warning message in case of malfunction of either system or cartridge. Additionally, processor 980 may transmit one or more questions to be displayed on display 982 that prompt a user to provide input in response thereto. Thus, in certain embodiments, input 984 and display 982 are integrated with one another. Processor 980 can be optionally further configured to transmit results of an analysis to an output device 986 such as a printer, a visual display, a display that utilizes a holographic projection, or a speaker, or a combination thereof. Processor 980 can be still further optionally connected via a communication interface such as a network interface to a computer network 988.

Processor 980 can be further configured to control various aspects of sample preparation and diagnosis, as follows in overview. In FIG. 11, the apparatus 981 is configured to operate in conjunction with a complementary rack 800. Apparatus 981 may be capable of receiving multiple racks, such as 1, 2, 3, 4, or 6 racks.

A rack 800 is itself configured, as further described herein, to receive a number of biological samples 996 in a form suitable for work-up and diagnostic analysis, and a number of holders 804—as further described herein, such as in connection with FIGS. 7A, 7B, that are equipped with various reagents, pipette tips and receptacles. The rack is configured so that, during sample work-up, samples are processed in the respective holders, the processing including being subjected, individually, to heating and cooling via heater assembly 977.

The heating functions of the heater assembly can be controlled by the processor 980. Heater assembly 977 operates in conjunction with a separator 978, such as a magnetic separator, that also can be controlled by processor 980 to move into and out of close proximity to one or more processing chambers associated with the holders 804, wherein particles such as magnetic particles are present.

Liquid dispenser 976, which similarly can be controlled by processor 980, is configured to carry out various suck and dispense operations on respective sample, fluids and reagents in the holders 804, to achieve extraction of nucleic acid from the samples. Liquid dispenser 976 can carry out such operations on multiple holders simultaneously. Sample reader 990 is configured to transmit identifying indicia about the sample, and in some instances the holder, to processor 980. In some embodiments a sample reader is attached to the liquid dispenser and can thereby read indicia about a sample above which the liquid dispenser is situated. In other embodiments the sample reader is not attached to the liquid dispenser and is independently movable, under control of the processor. Liquid dispenser 976 is also configured to take aliquots of fluid containing nucleic acid extracted from one or more samples and direct them to storage area 974, which may be a cooler. Area 974 contains, for example, a PCR tube corresponding to each sample.

Embodiments of the apparatus shown in outline in FIG. 8, as with other exemplary embodiments described herein, are advantageous because they do not require locations within the apparatus suitably configured for storage of reagents. Therefore, the apparatus in FIG. 8 is self-contained and operates in conjunction with holders 804, wherein the holders are prepackaged with reagents, such as in locations within it dedicated to reagent storage.

The apparatus of FIG. 8 may be configured to carry out operation in a single location, such as a laboratory setting, or may be portable so that they can accompany, e.g., a physician, or other healthcare professional, who may visit patients at different locations. The apparatus is typically provided with a power-cord so that they can accept AC power from a mains supply or generator. The apparatus may also be configured to operate by using one or more batteries and therefore is also typically equipped with a battery recharging system, and various warning devices that alert a user if battery power is becoming too low to reliably initiate or complete a diagnostic analysis.

The apparatus of FIG. 8 may further be configured, in other embodiments, for multiplexed sample analysis and/or analysis of multiple batches of samples, where, e.g., a single rack holds a single batch of samples. Each component shown in FIG. 8 may therefore be present as many times as there are batches of samples, though the various components may be configured in a common housing.

The apparatus herein can be configured to run on a laboratory benchtop, or similar environment, and can test approximately 45 samples per hour when run continuously throughout a normal working day. Results from individual raw samples are typically available in less than 1 hour.

EXAMPLES

Example 1

Reagent Holder

An exemplary reagent holder consistent with the description herein, and suitable for use with a rack as described herein, has the following dimensions and capacities:
- 180 mm long×22 mm wide×100 mm tall;
- Made from Polypropylene.
- One snapped-in low binding 1.7 ml tube that functions as a process tube.
- 3 built-in tubes that function as receptacles for reagents, as follows:
  - One tube containing 200-1000 µl of wash buffer (0.1 mM Tris, pH 8).
  - One tube containing 200-1000 µl of release solution (40 mM NaOH).
  - One tube containing 200-1000 µl of neutralization solution (330 mM Tris, pH 8.0).
- One built-in tube that functions as a waste chamber (will hold ~4 ml of liquid waste).
- 3 receptacles to accept containers for solid reagents. Snap-in 0.3 ml or 0.65 ml PCR tubes (which are typically stored separately from the reagent holder) are placed in each of these locations, and contain, respectively:
  - lyophilized sample preparation reagents (lysis enzyme mix and magnetic affinity beads).
  - First lyophilized PCR master mix, probes and primers for a first target analyte detection.
  - Second lyophilized PCR master mix, probes and primers for a second target analyte detection (only offered in select cases, such as detection of Chlamydia and Gonorrhea from urine).
- 4 pipette tips located in 4 respective sockets.
- Pipette tip Sheath: The pipette tips have a sheath/drip tray underneath to help capture any drip from the pipette tips after being used, and also to prevent unwanted contamination of the instrument.
- A mechanical key, in conjunction with a spring, allows easy insertion, removal, and positive location of strip in rack.
- One or more labels: positioned upward facing to facilitate ease of reading by eye and/or, e.g., a bar-code reader, the one or more labels containing human and machine readable information pertaining to the analysis to be performed.

It is to be understood that these dimensions are exemplary. However, it is particularly desirable to ensure that a holder does not exceed these dimensions so that a rack and an apparatus that accommodates the reagent holder(s) does not become inconveniently large, and can be suitably situated in a laboratory, e.g., on a bench-top.

Example 2

Exemplary Chemistry Processes Performed by an Automated Instrument

Sample Pre-Processing

For Urine Sample: Take 0.5 ml of urine and mix it with 0.5 ml of collection buffer. Filter the sample through a pre-filter (containing two membranes of 10 micron and 3 micron pore size). Place the sample tube in the position specified for the external sample tube in a 12-holder rack.

For Plasma Sample: Take 0.5 ml of plasma and mix it with 0.5 ml of collection buffer. Place the sample tube in the position specified for the external sample tube in the 12-holder rack.

For GBS swab samples: Take the swab sample and dip it in 1 ml of collection buffer. Place the sample tube in the position specified for the external sample tube in the 12-holder rack.

The sample collection buffer contains 50 mM Tris pH 7, 1% Triton X-100, 20 mM Citrate, 20 mM Borate, 100 mM EDTA, plus 1,000 copies of positive control DNA.

Loading the Instrument and Starting Sample Processing

The following steps may be performed to initiate an analysis on samples in batch.
1. Load PCR tube containing PCR master mix in one of the specified snap-in location of the reagent holder.
2. Load PCR tube containing PCR probes and primers for the target analyte under consideration in the specified location of the reagent holder.
3. In case of two analyte test, load PCR tube containing probes and primers for second analyte in the specified location of the reagent holder.
4. Insert the reagent holder in a 12-holder rack in the same lane as the sample tube under consideration.
5. Prepare and insert reagent holders for other samples in consideration.
6. Load the 12-holder rack in one of the locations in the instrument.
7. Load a 12-sample cartridge in the cartridge tray loading position.
8. Start operation.

Liquid Processing Steps

The following steps may be performed to carry out sample preparation.
1. Using Pipette tip #1, the robot transfers the clinical sample from the external sample tube to the process tube of the reagent holder.
2. Using the same pipette tip, the robot takes about 100 µl of sample, mixes the lyophilized enzyme and affinity beads, transfers the reagents to the process tube. Mixing is performed in the process tube by 5 suck and dispense operations.
3. The robot places pipette tip #1 at its designated location in the reagent holder.
4. Heat the process tube to 60° C. and maintain it for 10 minutes.
5. After 5 minute of lysis, the robot picks up pipette tip #1 and mixes the contents by 3 suck and dispense operations.
6. The robot places pipette tip #1 at its designated location in the reagent holder.
7. After 10 minutes of lysis, a magnet is moved up the side of the process tube to a middle height of the sample and held at that position for a minute to capture all the magnetic beads against the wall the tube.
8. The magnet is brought down slowly to slide the captured beads close to the bottom (but not the bottom) of the tube.
9. Using pipette tip #2, aspirate all the liquid and dump it into the waste tube.
10. Aspirate a second time to remove as much liquid as possible from the process tube.

11. Using the same pipette tip #2, withdraw 100 µl of wash buffer and dispense it in the process tube. During this dispense, the magnet is moved downwards, away from the process tube.
12. Perform 15 mix steps to thoroughly mix the magnetic beads with the wash buffer.
13. Wait for 30 seconds.
14. Move magnet up to capture the beads to the side and hold for 15 seconds.
15. Using pipette tip #2, aspirate wash buffer twice to remove as much liquid as possible and dump it back in the wash tube.
16. Move magnet down away from the process tube.
17. Place pipette tip #2 in its specified location of the reagent holder.
18. Pick up a new pipette tip (tip #3) and withdraw 8-10 µl of release buffer and dispense it over the beads in the process tube.
19. Wait for 1 minute and then perform 45 mixes.
20. Heat the release solution to 85° C. and maintain temperature for 5 minutes.
21. Place pipette tip #3 in its specified location of the reagent holder.
22. Bring magnet up the tube, capture all the beads against the tube wall and move it up and away from the bottom of the tube.
23. Pick up a new pipette tip (tip #4) and withdraw all the release buffer from the process tube and then withdraw 3-10 µl of neutralization buffer, mix it in the pipette tip and dispense it in the PCR tube. (In case of two analyte detections, dispense half of the neutralized DNA solution into first PCR tube and the rest of the solution in the second PCR tube.
24. Using pipette tip #4, mix the neutralized DNA with the lyophilized reagents by 4-5 suck and dispense operations and withdraw the entire solution in the pipette tip.
25. Using pipette tip #4, load 6 µl of the final PCR solution in a lane of the 12-up cartridge.

Real-Time PCR

After all the appropriate PCR lanes of the PCR cartridge are loaded with final PCR solution, the tray containing the cartridge moves it in the PCR Analyzer. The cartridge is pressed by an optical detection read-head against the PCR heater. Heaters activate valves to close either ends of the PCR reactor and real-time thermocycling process starts. After completing appropriate PCR cycles (~45 cycles), the analyzer decides whether the sample has the target DNA based on the output fluorescence data, and issues an indication of the same.

Example 3

Exemplary Rack

In an exemplary rack for use, in pairs, with a diagnostic instrument, disposable reagent holders (e.g., oriented orthogonally to the front of the instrument) can be contained in one of two, 12-lane racks. The 12 reagent holders in a given rack can register and lock into the rack upon insertion by a user. The rack contains an area for 12 sample lysis tubes and holds the tube bottoms co-planar, thereby allowing the user to orient a bar code on each tube to face the rear of the instrument.

Certain features, permit the racks to be inserted and oriented in the instrument by a minimally trained user. Proper rack placement can be confirmed by feedback to the software. In some embodiments, the racks can be black and color fast (e.g., the color may not appreciably degrade with use or washing with a 10% bleach solution) and the rack material can be dimensionally stable to within 0.1 mm over the operating temperature range of the system. The rack can be designed with provisions to allow the rack to be carried to and from the instrument and to minimize or eliminate the likelihood that the tubes held by the rack will spill when placed on a flat surface.

The foregoing description is intended to illustrate various aspects of the present inventions. It is not intended that the examples presented herein limit the scope of the present inventions. The technology now being fully described, it will be apparent to one of ordinary skill in the art that many changes and modifications can be made thereto without departing from the spirit or scope of the appended claims.

What is claimed is:

1. A rack, comprising:
a housing comprising a plurality of vertical members and a horizontal member, wherein the horizontal member comprises four corners and defines a top of the rack, wherein the vertical members extend vertically downward from the top of the rack, and wherein the horizontal member further comprises a first vertical side, a second vertical side, and a plurality of slots, each slot defining an opening in the first vertical side and extending in a direction towards the second vertical side;
a plurality of lanes in the housing, wherein each lane of the plurality of lanes comprises:
a first location adjacent to the second vertical side, the first location configured to accept a sample tube; and
a second location comprising one of the plurality of slots between the vertical members, the second location configured to accept a reagent holder comprising at least one reagent container and at least one process container, the housing configured to permit removal of the reagent holder from a lane without removing a sample tube from the lane; and
a registration member complementary to a receiving bay of a diagnostic apparatus, the registration member comprising at least two vertically downward extending pegs affixed to a bottom side of the horizontal member, wherein the vertical downward extension of the pegs is less than the vertical downward extension of the vertical members, wherein the pegs are configured to fixedly orient the rack within the diagnostic apparatus, wherein the pegs are located at least two corners of the housing, and wherein no corner includes more than one peg.

2. The rack of claim 1, further comprising a sensor actuator configured to indicate proper placement of the rack in the diagnostic apparatus.

3. The rack of claim 1, configured to be removed from the receiving bay of the diagnostic apparatus for loading of the sample tube and the reagent holder into the rack.

4. The rack of claim 1, further comprising a carrying handle.

5. The rack of claim 4, wherein the carrying handle is positioned about an axis displaced from an axis passing through the center of gravity of the rack when loaded, and is free to fall to a position flush with an upper surface of the rack, under its own weight.

6. The rack of claim 1, wherein the housing is made from aluminum.

7. The rack of claim 1, wherein the second location of each respective lane is a recessed portion within the horizontal member.

8. The rack of claim 7, wherein the two or more vertical members are configured to permit the rack to free stand.

9. The rack of claim 7, further comprising two or more feet, attached symmetrically to the first and second vertical members.

10. The rack of claim 7, wherein the housing further comprises a plurality of vertical spacer members, each of which is disposed between a pair of adjacent lanes.

11. The rack of claim 1, wherein at least a first lane and a second lane are parallel to one another.

12. The rack of claim 1, wherein pairs of adjacent sample lanes are separated by 24 mm at their respective midpoints.

13. The rack of claim 1, wherein the plurality of lanes consists of 2, 5, 6, 8, 10, 12, 16, 20, or 24 lanes.

14. The rack of claim 1, further comprising a lane identifier associated with each lane.

15. The rack of claim 1, wherein the first location comprises a recessed portion configured to receive a bottom of a sample tube, and an aperture configured to hold an upper portion of the sample tube.

16. The rack of claim 1, wherein the second location is a slot into which a reagent holder reversibly slides.

17. The rack of claim 1, wherein the second location is deep enough to accommodate one or more pipette tips.

18. The rack of claim 1, wherein a plurality of reagent holders in the plurality of lanes are maintained at the same height relative to one another.

19. The rack of claim 1, wherein the reagent holder contains sufficient reagents to extract polynucleotides from a sample and place the polynucleotides into a PCR-ready form.

20. A rack, comprising:
a housing comprising a horizontal member comprising a first vertical side, a second vertical side, a third vertical side, a fourth vertical side, and a plurality of slots between the third vertical side and the fourth vertical side, each slot defining an opening in the first vertical side and extending in a direction toward the second vertical side, the housing further comprising a plurality of lanes, each lane of the plurality of lanes comprising
a first location adjacent to the second vertical side and configured to accept a sample tube,
a second location comprising one of the plurality of slots; and
a reagent holder located in the second location, the reagent holder comprising
a process container,
a reagent container, wherein the reagent container is at least partially prefilled with a reagent, and
a pipette tip holder.

21. The rack of claim 20, wherein the reagent holder contains sufficient reagents to extract polynucleotides from a sample and place the polynucleotides into a PCR-ready form.

22. A rack, comprising:
a housing comprising a horizontal member, wherein the horizontal member comprises a first vertical side, a second vertical side, a third vertical side, a fourth vertical side, and a plurality of slots between the third vertical side and the fourth vertical side, each slot defining an opening in the first vertical side and extending in a direction toward the second vertical side;
a plurality of lanes in the housing, and wherein each lane of the plurality of lanes comprises:
a first location adjacent to the second vertical side and configured to accept a sample tube; and
a second location comprising one of the plurality of slots, the second location configured to accept a reagent holder comprising at least one reagent container and at least one process container, the housing configured to permit removal of the reagent holder from a lane without removing a sample tube from the lane; and
a registration member complementary to a receiving bay of a diagnostic apparatus.

23. The rack of claim 22, wherein each opening in the first vertical side is configured to accept a reagent holder slid horizontally into the corresponding slot.

24. The rack of claim 22, wherein each opening in the first vertical side is configured to permit removal of a reagent holder located in the corresponding slot.

25. The rack of claim 22, wherein each of the plurality of slots is configured to accept a reagent holder slid vertically into the slot.

26. The rack of claim 22, wherein each of the plurality of slots comprises a groove configured to engage a reagent holder.

27. The rack of claim 22, wherein the housing further comprises at least two vertical members extending vertically downward from the top of the rack.

28. The rack of claim 27, wherein the registration member comprises at least two vertically downward extending pegs affixed to a bottom side of the horizontal member, wherein the vertical downward extension of the pegs is less than the vertical downward extension of the vertical members, and wherein the pegs are configured to fixedly orient the rack within the diagnostic apparatus.

* * * * *

UNITED STATES PATENT AND TRADEMARK OFFICE
CERTIFICATE OF CORRECTION

PATENT NO. : 8,182,763 B2  Page 1 of 1
APPLICATION NO. : 12/178584
DATED : May 22, 2012
INVENTOR(S) : Duffy et al.

It is certified that error appears in the above-identified patent and that said Letters Patent is hereby corrected as shown below:

In column 3 at line 52, change "insertable," to --insertable--.

In column 18 at line 46, in Claim 1, before "at least" insert --at--.

Signed and Sealed this
Twenty-fifth Day of September, 2012

David J. Kappos
*Director of the United States Patent and Trademark Office*